US008181268B2

(12) United States Patent
Nakata et al.

(10) Patent No.: US 8,181,268 B2
(45) Date of Patent: May 15, 2012

(54) SCANNING PROBE MICROSCOPE AND METHOD OF OBSERVING SAMPLE USING THE SAME

(75) Inventors: Toshihiko Nakata, Hiratsuka (JP); Masahiro Watanabe, Yokohama (JP); Takashi Inoue, Yokohama (JP); Kishio Hidaka, Hitachiota (JP); Makoto Okai, Tokorozawa (JP); Toshiaki Morita, Hitachi (JP); Motoyuki Hirooka, Kumagaya (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/864,196

(22) PCT Filed: Dec. 18, 2008

(86) PCT No.: PCT/JP2008/073074
§ 371 (c)(1),
(2), (4) Date: Sep. 10, 2010

(87) PCT Pub. No.: WO2009/110157
PCT Pub. Date: Sep. 11, 2009

(65) Prior Publication Data
US 2010/0325761 A1    Dec. 23, 2010

(30) Foreign Application Priority Data

Mar. 5, 2008 (JP) ................................ 2008-054245
Sep. 30, 2008 (JP) ................................ 2008-252097

(51) Int. Cl.
*G01N 13/10* (2006.01)

(52) U.S. Cl. ................ 850/24; 850/22; 850/56; 850/58; 850/59

(58) Field of Classification Search .................... 850/22, 850/24, 56, 58, 59
See application file for complete search history.

(56) References Cited

U.S. PATENT DOCUMENTS

| 6,046,448 | A | 4/2000 | Sato et al. |
| 6,246,054 | B1 | 6/2001 | Toda et al. |
| 7,288,762 | B2 * | 10/2007 | Iyoki et al. ................... 250/306 |
| 7,543,482 | B2 | 6/2009 | Kitazawa et al. |
| 7,635,392 | B2 * | 12/2009 | Bloess et al. ................... 850/56 |
| 7,707,647 | B2 | 4/2010 | Konakahara |
| 7,945,966 | B2 * | 5/2011 | Minea et al. ................... 850/60 |
| 2006/0042321 | A1 | 3/2006 | Lewis et al. |

(Continued)

FOREIGN PATENT DOCUMENTS
JP            9-105865 A        4/1997
(Continued)

OTHER PUBLICATIONS

Togar Pangaribuan et al., "Reproducible Fabrication Technique of Nanometric Tip Diameter Fiber Probe for Photon Scanning Tunneling Microscope", Jpn. J. Appl. Phys., Sep. 1, 1992, pp. L1302-L1304, vol. 31, Part 2, No. 9A.

(Continued)

*Primary Examiner* — David A Vanore
(74) *Attorney, Agent, or Firm* — Crowell & Moring LLP

(57) ABSTRACT

Optical information and topographic information of the surface of a sample are measured at a nanometer-order resolution and with high reproducibility without damaging a probe and the sample by combining a nanometer-order cylindrical structure with a nanometer-order microstructure to form a plasmon intensifying near-field probe having a nanometer-order optical resolution and by repeating approach/retreat of the probe to/from each measurement point on the sample at a low contact force.

20 Claims, 30 Drawing Sheets

U.S. PATENT DOCUMENTS

| | | | |
|---|---|---|---|
| 2009/0020644 A1 | 1/2009 | Young et al. | |
| 2010/0031405 A1* | 2/2010 | Kley | 850/56 |
| 2010/0064396 A1* | 3/2010 | Nakata et al. | 850/30 |
| 2010/0218287 A1* | 8/2010 | Nakata et al. | 850/6 |
| 2010/0325761 A1* | 12/2010 | Nakata et al. | 850/33 |

FOREIGN PATENT DOCUMENTS

| | | |
|---|---|---|
| JP | 9-297099 A | 11/1997 |
| JP | 9-329605 A | 12/1997 |
| JP | 11-237391 A | 8/1999 |
| JP | 2002-267590 A | 9/2002 |
| JP | 2003-114184 A | 4/2003 |
| JP | 2003-337099 A | 11/2003 |
| JP | 2004-191277 A | 7/2004 |
| JP | 2005-249588 A | 9/2005 |
| JP | 2006-515682 A | 6/2006 |
| JP | 2008-275440 A | 11/2008 |
| WO | WO 2006/113192 A2 | 10/2006 |

OTHER PUBLICATIONS

Yasushi Inouye et al., "Near-Field Scanning Optical Microscope with a Metallic Probe Tip", Optics Letters, Feb. 1, 1994, pp. 159-161, vol. 19, No. 3.

Takayuki Okamoto, "Nano-Plasmonics", Studies on Spectroscopy, Jul. 11, 2005, pp. 225-237, vol. 54, No. 4.

International Search Report dated Jan. 27, 2009 (Two (2) pages).

* cited by examiner

| MATERIAL | $\lambda_1$ | $\lambda_2$ | $\lambda_3$ |
|---|---|---|---|
| Si | $I_{11}$ | $I_{21}$ | $I_{31}$ |
| $SiO_2$ | $I_{12}$ | $I_{22}$ | $I_{32}$ |
| $Si_3N_4$ | $I_{13}$ | $I_{23}$ | $I_{33}$ |
| Poly-Si | $I_{14}$ | $I_{24}$ | $I_{34}$ |
| W | $I_{15}$ | $I_{25}$ | $I_{35}$ |
| Aℓ | $I_{16}$ | $I_{26}$ | $I_{36}$ |
| Cu | $I_{17}$ | $I_{27}$ | $I_{37}$ |
| ⋮ | ⋮ | ⋮ | ⋮ |

SCANNING PROBE MICROSCOPE AND METHOD OF OBSERVING SAMPLE USING THE SAME

INCORPORATION BY REFERENCE

The present application claims the priorities of Japanese Patent Application No. 2008-054245 filed on Mar. 5, 2008 and Japanese Patent Application No. 2008-252097 filed on Sep. 30, 2008 and incorporates their contents by making reference to them.

TECHNICAL FIELD

The present invention relates to a scanning probe microscopic technique and a sample observing method using the same.

BACKGROUND ART

Scanning probe microscopes (SPM's) have been known as use for a technique of measuring three-dimensional nanostructures. Of them, an atomic force microscope (AFM) is for an observation technique in which the surface of a sample is scanned with a probe having a sharpened tip while controlling the contact force to a very small value and has been used widely as a technique capable of measuring three-dimensional nanostructures to atomic order. The atomic force microscope, however, cannot measure optical properties such as reflectance distribution and refractive index distribution of the sample surface.

On the other hand, in a microminiature semiconductor device of 45 nm or less node, the application of strained silicon is expected for speedup and so, measurement of a stress distribution in a micro-region is indispensable for yield control. For further miniaturization, the condition of impurity atom distribution is required to be managed delicately at a resolution of nanometer order. Physical properties information such as the stress distribution and impurity distribution cannot be measured with the atomic force microscope or a CD-SEM (Critical Dimension Scanning Electron Microscope) used for critical dimension control. An optical measure such as Raman spectroscopy has been studied but a typical Raman spectral microscope is insufficient for spatial resolution.

Further, in order to specify causes of generation of foreign particles detected through a foreign particle inspection and of defects detected through a defect inspection, classifying of foreign particles and defects is practiced with an electron microscope called a review SEM but this measure depends on the shape and surface profile information only and so, limits the classification performance. This measure can also be expected to improve the classification performance by adding optical information but the typical optical microscope and laser scanning microscope are still insufficient for spatial resolution.

As an expedient for solving the above problems and for measuring optical properties and physical properties information of the sample surface, a scanning near-field optical microscope (SNOM) has been known. In the microscope, by scanning near-field light leaking from a micro-aperture of several 10 nm while keeping a gap between the aperture and a sample held to the identical several 10 nm (aperture probe), optical properties such as reflective coefficient and refractive index of the sample surface are measured at a resolution of several 10 nm identical to the size of the aperture which is beyond the optical diffraction limit, as disclosed in Non-Patent Document 1. As a similar method, Non-Patent Document 2 also discloses a method in which light are irradiated on a metal probe from the outside and near-field light scattered at the micro-tip portion of the probe and having a size of several 10 nm are scanned (apertureless probe).

Further, Non-Patent Document 3 describes that a surface plasmon excited on a metal surface by a micro-spotlight propagates on the metal surface.

Patent Document 1 discloses a method of forming a micro-spotlight by forming a micro-spherical lens at the tip of a fiber.

Patent Document 2 discloses a method of obtaining a micro-spotlight by filling in the interior of a carbon-nanotube either the metal carbide such as V, Y, Ta, Sb or the like which exhibits photoluminescence or electro-luminescence or a ZnS fluorescent material or a CaS fluorescent material.

Patent Document 1:JP-A-2006-515682
Patent Document 2:JP-A-2002-267590
Non-Patent Document 1:Japanese Journal of Applied Physics, Vol. 31, pp. L1302-L1304 (1992)
Non-Patent Document 2:Optics Letters, Vol. 19, pp. 159-161 (1994)
Non-Patent Document 3:Studies on Spectroscopy, Vol. 54, No. 4, pp. 225~237 (2005)

DISCLOSURE OF THE INVENTION

Problem to be Solved by the Invention

The aforementioned scanning near-field microscope has a measurement resolution of several 10 nm order and is therefore, in comparison with the atomic force microscope and electron microscope each having a resolution of nm order, insufficient for the resolution by a single or more digit. Moreover, it involves such a problem fatal to industrial application that the measurement repeatability is very low. Namely, of the above methods, the method using the aperture probe has extreme difficulties in forming the aperture stably and practically, the limit is several 10 nm. In addition, when scanning on the sample, the probe collides with the sample and the aperture is damaged or worn and is gradually broadened, bringing about a reduction in repeatability of measurement images.

On the other hand, the apertureless probe using the metal probe is said as having a higher resolution than the aperture probe but the external illumination light scatters at the root of the probe or on the surface of a sample, resulting in background noise and like the aperture probe, when scanning on the sample, the probe collides with the sample and the tip is damaged or worn, giving rise to a problem that the measurement resolution is lowered and sufficient repeatability cannot be obtained.

In the method of forming a micro-spherical lens at the fiber tip end, the resolution is also several 10 nm or more in principle and when scanning on the sample, the spherical lens collides with the sample and is damaged or worn, so that the spotlight gradually grows up and its shape is deteriorated, bringing about degradation of repeatability of measurement images.

In the method of filling in the interior of carbon-nanotube the luminescent particles exhibiting photoluminescence or electro-luminescence, too, when the diameter of particle is of a nanometer order, the luminescent efficiency lowers to an extreme, making it difficult to obtain a near-field optical image at a high S/N ratio.

Accordingly, an object of the present invention is to provide a scanning probe microscope which can make possible the measurement of optical information and surface profile information of the sample at a resolution of nanometer order and at a high S/N ratio without damaging both the probe and the sample.

Another object of the present invention is to realize high-yield production of highly reliable semiconductor devices by measuring, at a resolution of nanometer order, physical properties such as stress distribution and impurity distribution of a semiconductor sample and optical information and surface profile information as well contributing to classifying of foreign particles and defects and by feeding them back to the production process condition.

To accomplish the above objects, a scanning probe microscope according to the present invention is constructed by comprising a measurement probe having its interior embedded with a metal structure, a cantilever for supporting the measurement probe, cantilever drive means for driving the cantilever to scan the measurement probe three-dimensionally in relation to an inspection objective sample, displacement detection means for detecting a distortion of the cantilever, and near-field optical image acquisition means for generating near-field light between the measurement probe embedded with the metal structure and the surface of the inspection objective sample and acquiring a near-field optical image of the inspection objective sample surface.

Structurally, AFM image generation means is further provided which generates an atomic force microscopic image (AFM image) of the surface of an inspection objective sample by processing a signal obtained by detecting a deformation of the cantilever with the help of displacement detection means.

Then, according to the present invention, in a method of observing a sample using a scanning probe microscope, a cantilever for supporting a measurement probe having its interior embedded with a metal structure is driven to scan the measurement probe three-dimensionally in relation to an inspection objective sample, a deformation of the cantilever attributable to the three-dimensional scan is detected optically, and a near-field optical image of the inspection objective sample surface is acquired using the measurement probe embedded with the metal structure.

Then, further, the signal obtained by detecting a deformation of the cantilever is processed to generate an atomic force microscopic image (AFM image) of the inspection objective sample surface.

According to the present invention, optical information and topographic information of the surface of a sample can be measured at a resolution of nanometer order and at a high S/N ratio without damaging both the probe and the sample. As a result, physical properties such as stress distribution and impurity distribution of a semiconductor sample can be measured and beside, optical information and surface profile information contributing to classifying of foreign particles and defects can be measured to improve the foreign particle/defect classification performance. Furthermore, by feeding the results of measurement back to the semiconductor production process condition, a highly reliable semiconductor device can be produced with high yield to advantage. Other objects, features and advantages of the invention will become apparent from a description of the following embodiments of the invention taken in conjunction with the accompanying drawings.

BEST MODE FOR CARRYING OUT THE INVENTION

As is known, when light is irradiated on a corpuscular metal particle, a surface plasmon is generated in which free electrons inside the metal are oscillated in a group and evanescent light generated on the surface of metal particle by the irradiated light couples with the surface plasmon, giving rise to a plasmon resonance, so that light absorption is caused and besides, an electric field significantly intensified locally is generated. In the present invention, a probe for generating at its tip the locally significantly intensified electric field (near-field light) is prepared and by using the probe, an optical properties of the sample surface is observed or measured.

Embodiments of the present invention will be described using drawings.

Embodiment 1

A first embodiment of the invention will be described on the basis of FIG. 1, FIGS. 9 to 12, and FIG. 23. In the present embodiment, as shown in FIG. 1, a multiwall carbon nanotube (CNT) 1 or a metal nanotube 1 is sharpened conically at its lower end and spherical nano-particles 2a and 2b of gold (Au) are filled in upper and lower ends of the hollow inner portion, respectively, thus forming a plasmon intensifying near-field probe. For example, when a voltage is applied across the both ends of the carbon nanotube and the applied voltage is increased, current reaches a saturation region in due time. With the applied voltage further increased, the current decreases stepwise and the nanotube is stripped sheet by sheet from the outer layer and thinned, being cut at the center of the nanotube eventually. Through this process, the tip of the nanotube can be sharpened. In a method of filling the gold nanoparticles, the nanotube 1 having its opposite ends opened by applying high voltage current or by heating, for example, and the gold nanoparticles 2 are located in a vacuum chamber and a capillary phenomenon is applied through heat reaction to enable the gold nanoparticles 2 to be involved inside the nanotube 1. For application of the capillary phenomenon, a technique disclosed on, for example, web (http://www1.accs-net.ne.jp/~kentaro/yuuki/nanotube/nanotube2.html) can be applied.

In the present embodiment, the nanotube has an outer diameter of 20 nm and the hollow portion has an inner diameter of 4 nm. Each of the nanoparticles 2a and 2b has a diameter of 4 nm. Then, a threshold of metal particle diameter necessary for generation of plasmon is said to be 1 nm or more and hence, as long as the diameter of gold nanoparticle is 1 nm or more, the object of the present invention can be accomplished. In the present embodiment, 4 nm is set as a limit of relatively stably producible gold nanoparticle diameter. But, in the invention, the diameter of gold nanoparticle is in no way limited to 4 nm and as long as the diameter falls within the range of approximately 1 nm to 20 nm, the object of the invention can be accomplished. In this case, the outer diameter of nanotube needs to be changed in accordance with the diameter of gold nanoparticle. In the embodiment as below, gold will be described as being used for the metal particle but even with a nanoparticle of another kind of metal, for example, a silver nanoparticle used, a similar effect can be attained.

This probe is molten and fixedly secured to an insulating holder designated at 6a, 6b under irradiation of an electron beam using tungsten (W) as binder, for example. Thereafter, from above a light guide 200 comprised of the insulating holder 6a, 6b and the gold nanoparticle 2a exposed to the upper end of the nanotube, laser beam 5a and 5b having a wavelength of 532 nm are converged by means of an objective lens 320 and irradiated. Through a plasmon resonance excited by the gold nanoparticle 2a induces a micro-spotlight. This micro-spotlight excites a surface plasmon in the nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and intensive local plasmon is excited in the gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light 8 turns into propagation light 9a and 9b which in turn are converged by the objective lens 320 to parallel light.

In the case of this probe, the plasmon directing from the light guide 200 or the upper end of nanotube 1 to the lower end thereof interferes with the plasmon directing in the inverse direction to generate a standing wave and there exist a node (at which the intensity is weak) and a antinode (at which the intensity is strong). The positions of the node and the antinode depend on the wavelength of the laser beam irradiated on the light guide 200. Accordingly, length L of the nanotube 1 is adjusted preferably such that the antinode of standing wave meets the lower end of nanotube 1 according to the wavelength of the laser beam.

FIG. 9 illustrates the construction of a scanning probe microscope carrying the present probe. The scanning probe microscope is constructed by comprising a stage unit 1000 movable in three-dimensional directions XYZ while carrying a sample, a measurement unit 2000 for measuring the sample by driving a nanotube 1 and processing obtained signals to generate an image, an illumination optical system 3000 for irradiating light necessary to generate near-field light between the tip of nanotube 1 and the sample, a detection optical system 4000 for detecting near-field light and converging and detecting propagation light, a sample monitor optical system 5000 for observing and positioning a portion to be measured on the sample and a controller 6000 for performing the entire control.

The stage unit 1000 has an XYZ stage 100 movable in three-dimensional directions of XYZ while carrying the sample and a driver 101. The sample 10 is mounted on the XYZ stage 100 and driven by the driver 101 so as to be positioned at a desired measurement location while observing the surface of sample 10 by means of the sample monitor optical system 5000 via the detection optical system 4000.

The measurement unit 2000 includes a light guide 200 and a cantilever 201 which are adapted to guide a laser beam to the nanotube 1, a piezoelectric device actuator 202, an XYZ piezoelectric device actuator 204, a semiconductor laser 206 for irradiating a laser beam (405 nm wavelength) 208 on the back of the cantilever 201, a quarter division position sensor 209 for detecting reflection light from the cantilever 201 and a drive circuit 207 for controlling the semiconductor laser.

The sample monitor optical system 5000 includes a mirror 500 capable of being inserted into/drawn out of an optical path of the detection optical system 4000 by a not shown drive means, and a pickup camera 501 for photographing an image of light having transmitted through an image forming lens 330 and having been reflected by the mirror 500. When setting a desired measurement location of sample 10 under the nanotube 1 by driving the XYZ stage 100 carrying the sample 10 by means of the driver 101, the mirror 500 is driven by a not shown drive means so as to be inserted into the optical path of detection optical system 4000, thus bending an optical path of reflection light from the sample to the pickup camera 501, and an optical image of the sample surface is observed with the pickup camera 501. With the desired measurement location of sample 10 positioned under the probe 1, the mirror 500 is driven by the not shown drive means so as to be retreated from the optical path of detection optical system 4000.

The nanotube 1 is fixed to the cantilever 201, together with the light guide 200 comprised of the insulating holder 4a, 4b and gold nanoparticle 2a shown in FIG. 1. The cantilever 201 is fixed to the piezoelectric device actuator 202 for its fine oscillation in Z directions and is also fixed to the XYZ piezoelectric device actuator 204 for its fine scanning in XYZ directions. A light beam emitted from a solid-state laser source 300 having a wavelength of 532 nm is halved by a beam splitter 302 of transmittance: reflectance=96:4 and reflected light 303 are received by a photoelectric conversion element 304 such as photodiode and converted thereby into an electric signal. This signal is sent to an entire control unit 420 in controller 6000 and used to monitor changes in intensity of the outgoing beam from the solid-state laser source 300 so as to control the output of solid-state laser source 300 to a constant intensity in the event that the intensity of outgoing beam changes.

The illumination optical system 3000 includes the laser source 300, a beam monitor optical system 3100, a beam shaping optical system 305, a polarization plate 307, a beam splitter 315 and an objective lens 320. With this construction, a beam 301 emitted from the laser source 300 and having transmitted through the beam splitter 302 of beam monitor optical system 3100 are converted into parallel light 306 of circular beam shape by means of the beam shaping optical system 305 and the converted light transmit through the polarization plate 307 and thereafter enter the beam splitter 315, followed by reflection at a circular reflection region 316b, by conversion to converged light 5a and 5b by means of the objective lens 320 and by irradiation on the upper end of nanotube 1 via the light guide 200.

In the measurement unit 2000, the converged light 5a and 5b incident to the gold nanoparticle 2a excite a plasmon resonance in the gold nanoparticle 2a, inducing a micro-spotlight as described previously. This micro-spotlight excites a surface plasmon in the nanotube 1 and the surface plasmon propagates through the nanotube 1 from its upper end to its lower end. Since the lower end of nanotube 1 is sharpened conically, the intensity of electric field is strengthened locally and an intensive local plasmon is excited in the nanoparticle 2b at the lower end of nanotube 1. The local plasmon interacts with the surface structure of sample 10 to generate an intensive resonance phenomenon, causing micro-near-field light spot 8. Reflection light from the near-field light 8 having interacted with the surface structure of sample 10 are converted into propagation light 9a and 9b. In the polarization plate 307, polarization axes 308 are formed radially (in radial direction) as shown in FIG. 10 and by controlling the polarization directions of the converged light 5a and 5b incident to the light guide 200 such that they are in parallel to the longitudinal direction of the nanotube 1, the excitation efficiency of plasmon and the propagation efficiency can be improved.

The detection optical system 4000 for detecting the propagation light 9a and 9b reflected from the sample includes the objective lens 330, the beam splitter 315, the image forming lens 330 and a photoelectric conversion element 340.

In the detection optical system 4000, the propagation light 9a and 9b are converged to parallel light which in turn transmit through a ring transmission region 316a of beam splitter 315 and transmitting light 90a and 90b are focused by the image forming lens 330 on the light receiving surface of photoelectric conversion element 340 such as photodiode or photomultiplier tube to undergo photoelectric conversion.

In an image forming unit 410 of measurement unit 2000, the detection signal from the photoelectric conversion element 340 is processed by using a control signal from a scanning control unit 400, adapted to generate a control signal for a driver 203 for driving the piezoelectric device actuator 202 and a control signal for a driver 205 for driving the XYZ piezoelectric device actuator 204, thus generating a two-dimensional near-field optical image and in addition, the output from the quarter division position sensor 209 is processed by using control signals for the drivers 203 and 205 for driving the piezoelectric device actuator 202 and the XYZ piezoelectric device actuator 204, thus generating an AFM image.

The two-dimensional near-field optical image and AFM image generated by the image forming unit 410 are sent to the entire control unit 420 in controller 6000 and they are displayed on separate output screens, respectively, or on the same output screen of an output unit 430 such as a display.

Next, it will be described by using the principle of optical lever how to determine a contact force when the nanotube probe 1 mounted on the end of cantilever 201 contacts the sample 10.

The laser beam (405 nm wavelength) 208 from the semiconductor laser 206 driven by the drive circuit 207 is irradiated on the back of the cantilever 201 and its reflection beam is received by the quarter division position sensor 209.

The XYZ piezoelectric device actuator 204 is driven by the driver 205 to lower the cantilever 201, bringing the nanotube 1 into contact with the sample 10. In this condition, as the cantilever 201 is further lowered, the inclination of the cantilever 201 changes and the reflection direction of the laser beam irradiated on the back of cantilever 201 changes, so that the incident position of the laser beam on the quarter division position sensor 209 changes and the output signal from the quarter division position sensor 209 changes. By comparing the changed signal with data of contact force determined in advance on the basis of the relation between the output signal from quarter division position sensor 209 and the inclination of cantilever 201, a contact force can be determined.

Next, procedures for measurement of the surface of sample will be described using FIG. 23. Firstly, the XYZ stage 100 is driven to position a measurement region of sample 10 under the nanotube 1 attached to the end of cantilever 201 (S2001). Subsequently, as shown in FIG. 11, while monitoring, in a measurement region of the sample 10, a contact state (contact force) of the nanotube 1 with the sample surface with the help of the output signal from the quarter division position sensor 209, the cantilever 201 is lowered by means of the XYZ piezoelectric device actuator 204 (Z direction scan 501) (S2002) and then, lowering is stopped at the time that a predetermined set contact force is reached (S2003).

After measurement of near-field light at a lowered point 502 has been completed (S2004), the cantilever 201 is raised (Z direction scan 503) (S2005) and if the nanotube 1 is determined as perfectly leaving the sample 10 on the basis of an output signal from the quarter division position sensor 209 (S2006), a decision is made as to whether the measurement of the measurement region ends (S2607) and if unfinished, the XYZ piezoelectric device actuator 204 is driven to move the cantilever 201 to the next measurement point (X scan 504) (S2009). The moving amount (feed pitch) in X scan is determined in accordance with a resolution required for observation. At the next measurement point, the cantilever 201 is again lowered and measurement of near-field light is carried out (S2002~S2006).

After the above step-in operation has been repeated over the two-dimensional measurement region (XY region) under the command of the XYZ piezoelectric device actuator 204, the measurement ends (S2007). Here, the method of measuring the two-dimensional measurement region is conducted through the same scanning as the raster scan in televisions. At that time, the feed pitch in Y direction (distance between adjacent scans) is determined in accordance with a resolution required for observation.

The XYZ direction scanning of XYZ piezoelectric device actuator 204 driven by the driver 205, the oscillation control of piezoelectric device actuator 202 driven by the driver 203 and the positioning of sample 10 by the XYZ stage 100 are collectively controlled by the scanning control unit 400 in measurement unit 2000 and the control of contact force of the nanotube 1 with the sample 10 and the measurement of near-field light are all controlled collectively by the entire control unit 420 in controller 6000. Each of the XYZ scanning signal for the XYZ piezoelectric device actuator 204 from scanning control unit 400 and the near-field light measurement signal from the entire control unit 420 is sent to the image forming unit 410, and the two-dimensional near-field optical image and the AFM image are generated which in turn are outputted to the output unit 430 such as display via the entire control unit 420 (S2008).

The relation between the contact force of the nanotube with the sample and the measurement timing is illustrated in FIG. 12. As indicated by a contact force change curve 510 at (a) in FIG. 12, as the nanotube 1 rises to retreat from the sample 10, the contact force shifts from pushing direction to draw-in direction and at an instant of leaving the sample, the draw-in force is maximized. After leaving, in the course of movement to the next measurement point and again approaching the sample, no contact force is received. When the nanotube 1 again begins approaching, a force in pushing direction is applied at an instant of contact to the sample 10 and at the time that the set contact force is reached, the cantilever 1 stops lowering.

On the other hand, as indicated by a detection light intensity curve 520 at (b) in FIG. 12, as the nanotube 1 rises to retreat from the sample 10, the near-field light detection intensity decreases gradually and takes a minimum value $I_F$ at an instant $T_F$ at which after the leaving from the sample, the retreat operation changes to the approach operation. Subsequently, the nanotube 1 again starts approaching and at an instant that the gold nanoparticle 2b comes into contact with the sample 10, the near-field light detection intensity takes a maximum value $I_C$ and the intensity $I_C$ is maintained while the set contact force is maintained. A difference $\Delta I = I_C - I_F$ between maximum value $I_C$ and minimum value $I_F$ at an arbitrary time $T_C$ during contacting is determined as a reflection light intensity at the measurement point, which in turn is stored in the entire control unit 420. By repeating the above operation over the two-dimensional measurement region, the reflectance distribution on the sample surface in the two-dimensional region can be measured at substantially the same optical resolution as that by the gold nanoparticle diameter 4 nm. Preferably, the set contact force is imparted by 1 nN or less, more preferably, by sub nN~pN.

In the present embodiment, the cantilever 201 does not undergo fine oscillation in Z direction but is subjected to lower and rise operation responsible for the set contact force. The detection of contact force is, however, not limited to the above optical lever method but the contact force can be detected from a change in oscillation amplitude or a change in oscillation frequency when the cantilever is finely oscillated in the Z direction by an amplitude of sub-nanometer order or at a frequency of MHz order.

As shown in FIGS. 1 and 12, according to the present embodiment, not only the AFM image and the near-field optical image can be captured simultaneously but also near-field light 8 of spot diameter 4 nm can constantly be generated stably between the gold nanoparticle 2b exposed to the lower end of nanotube 1 and the sample 10 and besides, by detecting near-field light 8 at an instant that the nanotube 1 is brought into contact with the sample 10 at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically.

(Modification 1 of Light Guide 200)

A modified example of the light guide 200 will be described on the basis of FIG. 2. FIG. 2 shows the structure of a plasmon intensifying near-field probe in the present embodiment. The structure of nanotube and its function are similar to those in the example shown in FIG. 1. In the first embodiment, the laser beam 5a and 5b of 532 nm wavelength are converged and irradiated from above the gold nanoparticle 2a exposed to the upper end of nanotube 1 and a plasmon resonance excited in the gold nanoparticle 2a excites a surface plasmon in the nanotube 1.

In contrast thereto, in the present modification, a gold wedge 3 is caused to approach, from above, a gold nanoparticle 2a exposed to the upper end of a nanotube 1 and laser beam 5a and 5b having a wavelength of 532 nm are converged and irradiated on the gold nanoparticle from above the gold wedge. Owing to a plasmon resonance excited between a tip end 3p of gold wedge 3 and the gold nanoparticle 2a, a micro-spotlight is induced. The micro-spotlight excites a surface plasmon in the gold nanoparticle 2a exposed to the upper end of nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and an intensive local plasmon is excited in a gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the nanotube 1 approaches the sample 10 most closely. In other words, with this probe, an optical resolution of 4 nm can be obtained and for example, regions 11 and 12 of different reflectance of the sample 10 can be discriminated from each other at this resolution.

According to the present modification, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample 10 at a low contact force, that is, the gold nanoparticle 2b comes into contact with the sample 10, stable detection of the near-field light rays can be achieved. As a result, the resolution of the two-dimensional near-field optical image can be improved and the repeatability of the image can be improved drastically. Further, in comparison with the case of the absence of the gold wedge 3, a more intensive plasmon resonance can be generated and consequently, the intensity of near-field light 8 increases and a near-field optical image of high S/N ratio can be obtained.

(Modification 2 of Light Guide 200)

A modified example of the light guide 200 will be described on the basis of FIG. 3. FIG. 3 shows the structure of a plasmon intensifying near-field probe in the present embodiment. The structure of nanotube and its function are similar to those in the example shown in FIG. 1. In the first modification, the gold wedge 3 is caused to approach, from above, the gold nanoparticle 2a exposed to the upper end of nanotube 1 and laser beam 5a and 5b having a wavelength of 532 nm are converged and irradiated from above the gold wedge to excite a plasmon resonance between the tip end 3p of gold wedge 3 and the gold nanoparticle 2a. In contrast thereto, in the present modification as shown in FIG. 3, a gold wedge 3 is caused to approach a gold nanoparticle 2a exposed to the upper end of a nanotube 1 laterally thereof and laser beam 5a and 5b having a wavelength of 532 nm are converged and irradiated from above the gold wedge, exciting a plasmon resonance between a tip end 3p of gold wedge 3 and the gold nanoparticle 2a. A micro-spotlight is induced by the plasmon resonance. The micro-spotlight excites a surface plasmon in the gold nanoparticle 2a exposed to the upper end of nanotube 1 and the surface plasmon propagates through the nanotube 1 from its upper end to lower end as shown at dotted arrows 7a and 7b. Since the lower end of nanotube 1 is sharpened conically, the intensity of electric field is strengthened locally and an intensive local plasmon is excited at a gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the nanotube 1 approaches the sample 10 most closely. In other words, with this probe, an optical resolution of 4 nm can be obtained and for example, regions 11 and 12 of different reflectance of the sample 10 can be discriminated from each other at this resolution.

According to the present modification, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample 10 at a low contact force, that is, the gold nanoparticle 2b comes into contact with the sample 10, stable detection of the near-field light 8 can be achieved. As a result, the resolution of the two-dimensional near-field optical image can be improved and the repeatability of the image can be improved drastically. Further, in comparison with the case of the absence of the gold wedge 3, a more intensive plasmon resonance can be generated and consequently, the intensity of near-field light 8 increases and a near-field optical image of high S/N ratio can be obtained.

(Modification 1 of Detection Optical System 4000)

A first modified example of the detection optical system 4000 according to the present invention will be described on the basis of FIG. 13. FIG. 13 shows the construction of a scanning probe microscope in the present embodiment. The scanning probe microscope has the basic construction and function similar to those of the scanning probe microscope in the embodiment shown in FIG. 9 but differs in that a spectrometer 611 is arranged as a section for detecting near-field light. Namely, near-field light 8 emanating from the lower end of a nanotube 1 and reflected at a sample 10 are converted into propagation light rays 9a and 9b which in turn are converted into parallel light 90a and 90b by an objective lens 320, the parallel light being converged by means of the image forming lens 330 on an incidence surface of the spectrometer 611 through the medium of a mirror 610.

In the spectrometer 611, light of a desired wavelength are selected from the propagation light on the basis of a control signal from the entire control unit 420 and they are converged on a light receiving surface of a photoelectric conversion element 612 such as photodiode, photomultiplier tube or the like so as to undergo photoelectric conversion. The detection signal is sent to the entire control unit 420 and a two-dimensional image of near-field light having a specified wavelength is formed. In the embodiment shown in FIG. 9 and its modification, the same wavelength as that of the incident laser beam is detected whereas in the present modification, near-field light having the wavelength shifted from that of the incident laser beam can be detected. For example, a stress distribution in a micro-field of a semiconductor device using strained silicon can be imaged at a resolution of nanometer by applying Raman spectroscopy. In this case, in order to prevent a Raman shift from being generated by a slight deformation of the sample itself due to contact with the nanotube 1, the contact force between nanotube 1 and sample 10 is preferably set to an order of nN~pN or less.

If a light source such as an LED having a broad wavelength band is used in place of a solid-state laser 300, a two-dimensional image of near-field light of an arbitrary wavelength within the wavelength band can also be detected. Further, if the spectrometer 611 is changed to an all wavelength collective detection type using an array sensor such as CCD one-dimensional sensor, a two-dimensional near-field optical image can also obtained, ensuring that spectroscopy of the sample 10 at a nanometer resolution can be carried out.

Like the embodiment shown in FIG. 9 and its modification, according to the present modification, not only the AFM image and the near-field optical image can be captured simultaneously but also near-field light 8 can constantly be generated stably and besides, stable detection of the near-field light can be achieved. As a result, the resolution of the two-dimensional near-field optical image can be improved and the repeatability of the image can be improved drastically.

(Modification 2 of Detection Optical System 4000)

A second modified example of the detection optical system 4000 will be described on the basis of FIG. 14. In FIG. 14, a white light laser 620 emitting a three-color beam near wavelengths 630 nm, 520 nm and 430 nm is used as light source 620 and color separation filters 625r, 625g and 625b are arranged in the section for detection of near-field light. A process ranging from generation of near-field light 8 between nanotube 1 and sample 10 by a laser beam emitted from the light source 620 to transmission of propagation light 9a and 9b of reflection of the laser beam through objective lens 320 and beam splitter 315 and ultimate arrival at the image forming lens 330 is the same as that described using FIG. 9.

Parallel light 90a and 90b reaching the objective lens 330 are converged by the image forming lens 330 and, through the medium of a mirror 610, converted into parallel light by a relay lens 615 and then, light of wavelength 630 nm are extracted by means of a dichroic mirror 621 (for transmission of wavelength of 600 nm or more and reflection of wavelengths of less than 600 nm) and the interference filter 625r (630 nm transmission center wavelength). The light are converged by means of a condenser lens 631 on the light receiving surface of photoelectric conversion element 641 such as photodiode or photomultiplier tube so as to be photoelectrically converted. Light reflected by the dichroic mirror 621 are processed by a dichroic mirror 622 (reflection for wavelengths of more than 480 nm and transmission for less than 480 nm wavelengths) and an interference filter 625g (520 nm transmission center wavelength), so that light of 520 nm wavelength are extracted. The light are converged by means of a condenser lens 632 on the light receiving surface of a photoelectric conversion element 642 such as photodiode or photomultiplier tube so as to be converted photoelectrically. Light having transmitted through the dichroic mirror 622 are reflected by a mirror 623 and thereafter light of 430 nm wavelength are extracted by means of an interference filter 625b (430 nm transmission center wavelength). The light are converged by means of a condenser lens 633 on the light receiving surface of a photoelectric conversion element 643 such as photodiode or photomultiplier tube so as to be converted photoelectrically.

The detection signals of 3 wavelengths are sent to the entire control unit 420 and two-dimensional near-field optical images of 3 wavelengths are formed. By synthesizing the three-wavelength signals, a color image can also be generated at a nanometer resolution. According to the present embodiment, for example, a defect review for semiconductor carried out at present by classifying defects from only a monochromatic image with the help of an SEM can be practiced by using an AFM image and a color image at nanometer resolutions and the accuracy of defect classification can be improved drastically. According to the present modification, not only the AFM image and the near-field optical image can be acquired simultaneously but also near-field light 8 can constantly be generated stably and stable detection of the near-field light can be achieved. As a result, the resolution of the two-dimensional near-field optical image can be improved and the repeatability of the image can be improved drastically (Modification 1 of Measurement Unit 2000)

A first modified example of the measurement unit 2000 according to the invention will be described on the basis of FIG. 15. FIG. 15 illustrates a changed portion of measurement unit 2000 according to the present embodiment. In the present construction, a memory unit 440 is added to the construction shown in FIG. 14, which memory unit stores sets of semiconductor material/spectroscopic reflectance data as shown in table 441 of FIG. 16 (in the illustration of FIG. 15, components common to those shown in FIG. 14 are omitted extensively). More particularly, as shown in FIG. 16, pieces of data $I_{21}, I_{31}), (I_{12}, I_{22}, I_{32}), (I_{13}, I_{23}, I_{33})$ ... of combinations of various materials used for semiconductor production such as Si and $SiO_2$ with reflection light intensities for individual light source wavelengths $\lambda_1$=630 nm, $\lambda_2$=520 nm and $\lambda_3$=430 nm are stored in advance in the memory unit 440 and obtained detection light intensities of 3 wavelengths are collated with the table 441 to execute determination of a material constituting the sample 10 at a nanometer spatial resolution. Of course, the wavelengths are not limited to 3 wavelengths but may be increased to 4 wavelengths or 5 wavelengths to improve the accuracy of material analysis.

FIG. 17 illustrates an example where the scanning probe microscope in the present modification is applied to detection of a film left behind at the bottom end of a deep hole such as contact hole. By inserting a nanotube 1 into the interior of a contact hole 501 of a diameter of about 30 nm, capturing a spectroscopic signal at an instant that the nanotube comes into contact with the hole bottom end at a low contact force and collating the spectroscopic signal with the relation between the film thickness and the spectroscopic intensity stored in advance in the memory unit 440, information as to the presence or absence of a residual film 502 and its material can be obtained.

According to the present modification, not only the AFM image and the near-field optical image can be captured simultaneously but also near-field light can constantly be generated stably and stable detection of the near-field light can be achieved. As a result, the resolution of the two-dimensional near-field optical image can be improved and the repeatability of the image can be improved drastically (Modification 2 of Measurement Unit 2000)

A first modified example of the measurement unit 2000 according to the invention will be described on the basis of FIG. 18. FIG. 18 illustrates the construction of a scanning probe microscope according to the present embodiment. The present scanning probe microscope has the basic construction and function similar to those of the scanning probe microscope in the embodiment shown in FIG. 9 but differs in that a cantilever 201 is finely oscillated in Z direction. The piezoelectric device actuator 202 is driven by the driver 203 to finely oscillate the cantilever 201 in Z direction at a constant frequency f, thus applying intensity modulation to near-field light 8. By using the drive signal at the constant frequency f as a reference signal, a lock-in amplifier 450 extracts only a component of frequency f from the detection signal of photoelectric conversion element 340, making it possible to detect information of near-field light 8 with high sensitivity. An output signal from the lock-in amplifier 450 is sent to the entire control unit 420. The ensuing procedures are similar to those in the scanning probe microscope in the embodiment shown in FIG. 9.

According to the present modification, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample 10 at a low contact force, that is, the gold nanoparticle 2b comes into contact with the sample 10, stable detection of the near-field light rays can be achieved. As a result, the resolution of the two-dimensional near-field optical image can be improved and the repeatability of the image can be improved drastically. Further, through the lock-in detection of the near-field light 8, a near-field optical image of high S/N ratio can be obtained.

Embodiment 2

A second embodiment of the present invention will be described on the basis of FIGS. 4 and 19. FIG. 4 illustrates the structure of a plasmon intensifying near-field probe in the present embodiment. Like the first embodiment and its modifications, the nanotube is a multiwall carbon nanotube 1 or a metal nanotube 1, having the lower end sharpened conically. In the first embodiment and its modifications, gold (Au) spherical nanoparticles 2a and 2b are filled in the upper end and lower end of an interior hollow portion whereas in the present embodiment, as shown in FIG. 4, a fluorescent particle 25 of either metal carbide such as V, Y, Ta, Sb or the like exhibiting photoluminescence or electro-luminescence, or ZnS fluorescent material, CaS fluorescent material or CdSe (core)/ZnS (outer shell) is carried above the gold nanoparticle 2a at the upper end, thus structuring a light guide 200.

FIG. 19 illustrates the construction of a scanning probe microscope carrying the present probe. The present scanning probe microscope has the basic construction and function similar to those of the scanning probe microscope in the embodiment shown in FIG. 9 but differs in 25 that a wavelength selection filter 355 having a transmission band for (a fluorescent wavelength at which the fluorescent particle fluoresces) ±10 nm is arranged immediately before the a photoelectric conversion element 340 such as photodiode or photomultiplier tube for detection of near-field light. More particularly, as shown in FIG. 4, when laser beam 5a and 5b emitted from the solid-state laser 300 are converged and irradiated on the fluorescent particle 25a, fluorescence having a wavelength different from that of the laser beam 5a and 5b is generated. This fluorescence generates a plasmon resonance in the gold nanoparticle 2a, inducing a micro-spotlight having the same wavelength as that of the fluorescence. The micro-spotlight excites a surface plasmon in the nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and an intensive local plasmon is excited at the gold nanoparticle 2b at the lower end of nanotube 1. The local plasmon interacts with the surface structure of the sample 10 to generate an intensive resonance phenomenon, causing micro-near-field light spot 8 of the same wavelength as that of the fluorescence.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light 8 turns into propagation light 9a and 9b which in turn are converged by objective lens 320 to parallel light 90a and 90b. The parallel light 90a and 90b transmit through the ring band transmission region 316a of beam splitter 315, transmitted light propagates through the image forming lens 330 and then, by the wavelength selection filter 355, only a fluorescent wavelength component 318 is extracted which in turn is photoelectrically converted by the photoelectric conversion element 340 such as photodiode or photomultiplier tube. The ensuing procedures are similar to those in the scanning probe microscope in the embodiment shown in FIG. 9.

To add, in the present embodiment, the fluorescent particle 25 is used for the light guide 200 but this is not limitative and for example, by using a non-linear optical crystal, near-field light having a wavelength half the wavelength of the incident beam can be generated.

According to the present embodiment, not only the AFM image and the near-field optical image can be acquired simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically. Further, according to the present embodiment, scattering light and background noise caused by the laser beam 5a and 5b emitted from the solid-state laser 300 on the midway optical path and in the nanotube itself can be reduced to a great extent and so a near-field optical image of high S/N ratio can be obtained.

Embodiment 3

A third embodiment of the present invention will be described on the basis of FIGS. 5 and 20. FIG. 5 illustrates the structure of a plasmon intensifying near-field probe in the present embodiment. Like the first embodiment and its modifications, the nanotube is a multiwall carbon nanotube 1 or a metal nanotube 1, having the lower end sharpened conically and having gold (Au) spherical nanoparticles 2a and 2b filled in the upper end and lower end of an interior hollow portion. While in the first and second embodiments and its modifications, laser beam are converged and irradiated on the gold nanoparticle 2a exposed to the upper end of nanotube 1 from above the nanoparticle 2a, the present embodiment differs in that a light guide 200 is such that laser beam 16 linearly polarized in a direction 17 parallel to the longitudinal direction of nanotube 1 are converged laterally of the nanotube by means a condenser lens 5 and irradiated as shown in FIG. 5.

FIG. 20 illustrates the construction of a scanning probe microscope carrying the present probe. The present scanning probe microscope has the basic construction and function similar to those of the scanning probe microscope in the embodiment shown in FIG. 9 but differs in that in place of the illumination optical system 3000 for converging and irradiating laser beam on a gold nanoparticle 2a exposed to the upper end of nanotube 1 from above the nanoparticle 2a, an illumination optical system 700 is mounted which incorporates a laser source adapted for conversing and irradiating laser beam laterally of the nanotube 1 as shown in FIG. 5. In the illumination optical system 700, a monitor signal for the laser beam is additionally sent to the entire control unit 420 and when the intensity of the laser beam changes, the output of the laser beam source is controlled to make the intensity constant.

By a plasmon resonance excited by the gold nanoparticle 2a, a micro-spotlight is induced. The micro-spotlight excites a surface plasmon in the nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light 8 turns into propagation light 9a and 9b which in turn are converged by objective lens 320 to parallel light 90a and 90b. The parallel light 90a and 90b transmit through the ring band transmission region 316a of beam splitter 315, transmitted light propagates through the image forming lens 330 and they are converted photoelectrically by the photoelectric conversion element 340 such as photodiode or photomultiplier tube. The ensuing procedures are similar to those in the scanning probe microscope in the embodiment shown in FIG. 9.

According to the present embodiment, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically.

(Modification of Light Guide 200)

A modified embodiment of the light guide 200 will be described on the basis of FIG. 6. FIG. 6 illustrates the structure of a plasmon intensifying near-field probe in the present embodiment. The structure and function of a nanotube 1 is similar to those in the example shown in FIG. 1. In the third embodiment, the light guide 200 is structured in which a laser beam 16 linearly polarized in a direction 17 parallel to the longitudinal direction of the nanotube 1 are converged laterally of the nanotube by means of a condenser lens 15 and irradiated on the gold nanoparticle 2a exposed to the upper end of nanotube 1. In contrast thereto, in the present modification, a nanotube holder designated at 21a, 21b is formed from a gold or silver cylindrical rod and is used as a light guide 200. The linear polarization laser beam 16 in the direction 17 parallel to the longitudinal direction of nanotube 1 are converged and irradiated on the nanotube holder 21a, 21b laterally thereof by the condenser lens 5.

Under the irradiation of the linear polarization laser beam 16, a surface plasmon is excited in the cylindrical nanotube holder designated at 21a, 21b made of gold or silver and it propagates in the nanotube longitudinal direction, so that a plasmon is excited in a gold nanoparticle 2a and a micro-spotlight is induced. The micro-spotlight excites a surface plasmon in the nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light spot 8. With the gold nanoparticle 2a omitted, a plasmon can be excited and propagated in nanotube 1 directly from the cylindrical nanotube holder 21a, 21b.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light 8 turns into propagation light 9a and 9b which in turn are converged by objective lens 320 to parallel light 90a and 90b. The parallel light 90a and 90b transmit through the ring band transmission region 316a of beam splitter 315, transmitted light propagates through the image forming lens 330 and they are photoelectrically converted by the photoelectric conversion element 340 such as photodiode or photomultiplier tube. The ensuing procedures are similar to those in the scanning probe microscope in the embodiment shown in FIG. 9.

According to the present embodiment, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically.

Embodiment 4

A fourth embodiment of the present invention will be described on the basis of FIGS. 7 and 21. FIG. 7 illustrates the structure of a plasmon intensifying near-field probe in the present embodiment. Like the first embodiment and its modifications, the nanotube is a multiwall carbon nanotube 1 or a metal nanotube 1, having the lower end sharpened conically and having gold (Au) spherical nanoparticles 2a and 2b filled in the upper end and lower end of an interior hollow portion.

In the present embodiment, as shown in FIG. 7, the illumination optical system 3000 is excluded thoroughly and a light guide 200 is structured by carrying a laser source 27 such as semiconductor laser (for example, 405 nm wavelength) on a gold nanoparticle 2a at the upper end of nanotube 1.

FIG. 21 illustrates the construction of a scanning probe microscope carrying the present probe. The present scanning probe microscope has the basic construction and function substantially similar to those of the scanning probe microscope in the embodiment shown in FIG. 9 but differs in that the illumination optical system 3000 is excluded thoroughly and a light guide 200 carrying the laser source 27 such as semiconductor laser is disposed above the gold nanoparticle 2a at the upper end of a nanotube 1. The laser source 27 is driven by a drive signal 720 from the drive circuit 710 and a monitor signal for the laser beam is sent to the entire control unit 420 so that when the intensity of the laser beam changes, the intensity may be made to be constant by controlling the output of the laser source.

A plasmon is excited in the gold nanoparticle 2a irradiated with the laser source 27 and a micro-spotlight is induced. The micro-spotlight excites a surface plasmon in the nanotube 1 and the surface plasmon propagates through the nanotube 1 from its upper end to lower end as shown at dotted arrows 7a and 7b. Since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light 8 turns into propagation light 9a and 9b which in turn are converged by objective lens 320 to parallel light 90a and 90b. The parallel light 90a and 90b transmit through the ring band transmission region 316a of beam splitter 315, transmitted light propagates through the image forming lens 330 and they are converted photoelectrically by the photoelectric conversion element 340 such as photodiode or photomultiplier tube. The ensuing procedures are similar to those in the scanning probe microscope in the embodiment shown in FIG. 9.

According to the present embodiment, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically. Further, according to the present embodiment, the illumination optical system 3000 can be dispensed with to simplify the construction of the scanning probe microscope and at the same time, the efficiency of excitation/propagation of the plasmon can be improved by the nearby laser beam source and a near-field optical image of high S/N ratio can be obtained.

Embodiment 5

A fifth embodiment of the present invention will be described on the basis of FIGS. 8 and 22. FIG. 8 illustrates the structure of a plasmon intensifying near-field probe in the present embodiment. Like the first embodiment and its modifications, the nanotube is a multiwall carbon nanotube 1 or a metal nanotube 1, having the lower end sharpened conically and having gold (Au) spherical nanoparticles 2a and 2b filled in the upper end and lower end of an interior hollow portion. In the present embodiment, as shown in FIG. 8, the illumination optical system 3000 is excluded thoroughly and an optical system is constructed in which a laser beam from a semiconductor laser (for example, 405 nm wavelength) 730 or solid-state laser 730 is guided by an optical fiber 30 so as to be irradiated by means of the condenser lens 31 on a gold nanoparticle 2a at the upper end of nanotube 1 through a polarization plate 307, and the optical system is used as the light guide 200.

FIG. 22 illustrates the construction of a scanning probe microscope carrying the present probe. The present scanning probe microscope has the basic construction and function substantially similar to those of the scanning probe microscope in the embodiment shown in FIG. 9 but differs in that the illumination optical system 3000 is thoroughly excluded and a light guide 200 is arranged which includes the laser beam source 730, optical fiber 30, condenser lens 31 and polarization plate 307. A monitor signal for the laser beam from the laser beam source 730 is sent to the entire control unit 420 and when the intensity of the laser beam changes, the intensity may be made to be constant by controlling the output of the laser source 730.

A plasmon is excited in the gold nanoparticle 2a irradiated with the laser beam 32 from optical fiber 30 and a micro-spotlight is induced. The micro-spotlight excites a surface plasmon in the nanotube 1 and the surface plasmon propagates through the nanotube 1 from upper end to lower end as shown at dotted arrows 7a and 7b. Since the lower end of nanotube 1 is sharpened conically, the intensity of electric field is strengthened locally and intensive local plasmon is excited in the gold nanoparticle 2b at the lower end of nanotube 1. The local plasmon interacts with the surface structure of the sample 10 to generate an intensive resonance phenomenon, causing micro-near-field light spot 8.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained and for example, regions 11 and 12 of different reflectance of the sample 10 can be discriminated from each other at this resolution. With the atomic force microscope, the regions 11 and 12 cannot be discriminated. Reflection light of near-field light light 8 turns into propagation light 9a and 9b which in turn are converged by objective lens 320 to parallel light rays 90a and 90b. The parallel light 90a and 90b transmit through the ring band transmission region 316a of beam splitter 315, transmitted light propagates through the image forming lens 330 and they are converted photoelectrically by the photoelectric conversion element 340 such as photodiode or photomultiplier tube. The ensuing procedures are similar to those in the scanning probe microscope in the embodiment shown in FIG. 9.

According to the present embodiment, not only the AFM image and the near-field optical image can be captured simultaneously but also near-field light 8 of spot diameter 4 nm can constantly be generated stably between the gold nanoparticle 2b at the lower end of nanotube 1 and the sample 10 and besides, by detecting near-field light 8 at an instant that the nanotube 1 is brought into contact with the sample at a low contact force, that is, the gold nanoparticle 2b comes into contact with the sample 10, stable detection of the near-field light can be achieved. As a result, the resolution of the two-dimensional near-field optical image can be improved and the repeatability of the image can be improved drastically. Further, according to the present embodiment, the illumination optical system 3000 can be dispensed with to simplify the construction of the scanning probe microscope.

To add, in the foregoing first to fifth embodiments, a gold nanoparticle is used as the nanoparticle but the present invention is not limited thereto and a nanoparticle of for example, silver or aluminum can be applicable as long as the particle has high efficiency from the standpoint of plasmon excitation and plasmon propagation. Also, the nanotube is not limited to the multiwall carbon nanotube or metal nanotube but another material and another structure may be employed provided that they are similar to a cylindrical structure or the like of nanometer order diameter such as a single-wall carbon nanotube or a metal containing carbon nanotube and when combined with the aforementioned nanoparticle, suitable for plasmon excitation and plasmon propagation.

Further, in the first to fifth embodiments, the plasmon excitation wavelength is set to 532 nm or 405 nm but the present invention is not limited thereto and from the standpoint of plasmon excitation and plasmon propagation, a wavelength efficient for the length of the nanotube which is considered as a resonator (resonance wavelength) may preferably be used.

Further, the foregoing first to fifth embodiments are constructed such that for detection of near-field light, propagation light from the surface of the sample at the lower end of nanotube are detected but the invention is not limited thereto and obviously, when the plasmon propagates from lower end to upper end of the nanotube, propagation light scattering at the upper end may be detected.

Embodiment 6

A sixth embodiment of the present invention will be described on the basis of FIGS. 24, 25, 27, 28, 30 and 31. FIG. 24 illustrates the structure of a light guide for a plasmon intensifying near-field probe in the present embodiment. In the first to fifth embodiments, the light guide 200 for guiding excited light to the nanotube 1 is disposed in the rear of the cantilever 201 but in the present embodiment, a cantilever 201 itself is used for a light guide. At the end of the cantilever 201 made of, for example, Si, a tip 730 of triangular pyramid shape similarly made of Si is formed and a nanotube 1 is fixed to the end of tip 730. On a back surface 201s of cantilever 1, propagated excitation light 5a and 5b are converged and irradiated. This situation will be described in detail using a sectional diagram of cantilever 201 and tip 730 shown in FIG. 25. When both the cantilever 201 and the tip 730 are made of Si, a near infrared laser beam of, for example, 830 nm wavelength is used for the excitation light 5a and 5b which in turn are converged with the help of a NA (Numerical Aperture) of 0.2 and irradiated on the back surface 201s of cantilever 201. The polarization direction 5p is P polarization and the converging angle 735 is about 23°. With a view to suppressing the loss of light quantity due to surface reflection, the incident angle 736 is preferably about 75° which is the Brewster angle. Incident excitation light is refracted and converged on a edge line 730w of triangular pyramid tip 730. The converging angle 737 is about 6°. The incident angle to the edge line 730w is preferably set to more than about 16° which is the critical angle. The surface of tip 730 are coated with gold thin films 730f and 730r. In consideration of the efficiency of generation of plasmon, the film thickness of the gold thin film 730f along the edge line 730w is about 50 nm and the thickness of two slant surfaces sandwiching the edge line 730w is preferable thinner than the former thickness. With the P polarized excitation light irradiated on the edge line 730w, a TM (Transverse Magnetic) mode plasmon 740 is excited along the surface of the metal thin film 730f and it propagates towards the end of tip 730. The permissible range of resonance dip incident angle 738 for excitation of the plasmon is 2°~3° at the most and therefore, the range of converging angle 737 of excitation light is preferably about 6° which is twice the former angle mentioned as above. The excited TM mode plasmon 740 propagates as shown at dotted arrows 7a and 7b in FIG. 27 from upper end to lower end along the surface of the nanotube 1 fixed to the end of tip 730 and by way of gold nanoparticles 2a, 2c and 2b filled in the interior of the nanotube. Like the first embodiment and its modifications, the nanotube is a multiwall carbon nanotube 1 or a metal nanotube 1, having its lower end sharpened conically. As shown in FIG. 27, since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light spot 8.

In the present embodiment, the nanotube has an outer diameter of 20 nm and the hollow portion has an inner diameter of 4 nm. Each of the nanoparticles 2a, 2b and 2c has a diameter of 4 nm. Then, the limit of metal particle diameter necessary for generation of plasmon is said to be 1 nm or more and hence, as long as the diameter of gold nanoparticle is 1 nm or more, the object of the present invention can be accomplished. In the present embodiment, 4 nm is set as a limit of relatively stably producible gold nanoparticle diameter. But, in the invention, the diameter of gold nanoparticle is in no way limited to 4 nm and as long as the diameter falls within the range of approximately 1 nm to 20 nm, the object of the invention can be accomplished. In this case, the outer diameter of nanotube needs to be changed in accordance with the diameter of gold nanoparticle. In the embodiment as below, gold will be described as being used for the metal particle but even with a nanoparticle of another kind of metal, for example, a silver nanoparticle used, a similar effect can be attained.

The spot diameter of the near-field light 8 becomes 4 nm substantially equal to the size of gold nanoparticle 2b when the gold nanoparticle 2b approaches the sample 10 most closely. In other words, with this probe, an optical resolution of 4 nm can be obtained. In the present embodiment, the gold nanoparticle array is shown as the metal structure filled in the nanotube 1 but the invention is not limited thereto and similar effects can be attained even by filling a gold nanorod 702, for example, as shown in FIG. 28. The material of the nanorod may be another kind of metal and even with a silver nanorod, for example, a similar effect can be attained. Further, even with the structure in which the gold nanoparticles 2a and 2b are filled in only the upper end and lower end of the nanotube 1 as shown in the first to fifth embodiments, similar effects can be attained.

While in the present embodiment the cantilever 201 and tip 730 are made of Si, the present invention is not limited thereto and the cantilever 201 and tip 730 made of, for example, $Si_3N_4$ can also be applied. In this case, as the excitation light, visible light of, for example, wavelength 532 nm can be used. Visible laser beam of 532 nm wavelength are converged with the help of a NA (Numerical Aperture) of 0.1 and irradiated on the back surface 201s of cantilever 201. The polarization direction 5p is P polarization and the converging angle 735 is about 11.5°. With a view to suppressing the loss of light quantity due to surface reflection, the incident angle 736 is preferably about 63° which is the Brewster angle. Incident excitation light is refracted and converged on the edge line 730w of triangular pyramid tip 730. The converging angle 737 is about 5.7°. The incident angle 738 to the edge line 730w is preferably set to more than about 30° which is the critical angle.

In the case of this probe, the plasmon directing from the upper end of nanotube 1 to the lower end thereof interferes with the plasmon directing in the inverse direction to generate a standing wave and there exist a node (at which the intensity is weak) and a antinode (at which the intensity is strong). The positions of the node and the antinode depend on the wavelength of the laser beam irradiated on the light guide 200. Accordingly, the length L of nanotube 1 is adjusted preferably such that the antinode of standing wave meets the lower end of nanotube 1 according to the wavelength of the laser beam.

FIG. 30 illustrates the construction of a scanning probe microscope carrying the present probe. The construction and function of the present scanning probe microscope is similar to those in the first embodiment shown in FIG. 9 and its description will be omitted. To add, in FIG. 9, the light guide quarter 200 for guiding the excitation light rays to the nanotube 1 is disposed in the rear of cantilever 201 but in the present embodiment, the cantilever 201 itself impersonates the light guide quarter and therefore, the light guide quarter 200 is structurally excluded as shown in FIG. 30. Further, since the excitation light rays 5a and 5b are P polarization light rays in relation to the back surface of cantilever 201, the polarization plate 307 is also excluded structurally.

Preferably, the wavelength of excitation light rays 5a and 5b is not fixed to 830 nm but is finely adjusted to a wavelength at which the excited TM mode plasmon 740 can propagate to the nanotube 1 without loss, that is, with high coupling efficiency. For example, with a white light laser used, an optimum coupling wavelength is selected for the excitation light ray, or a white light laser beam is used as the excitation light ray and preferably only an optimum coupling wavelength is selectively detected by a wavelength selection filter disposed immediately before the photoelectric conversion element 340. In FIG. 25, TM mode plasmon 740 failing to couple with the nanotube 1 turns into near-field light rays at the tip end of tip 730 and these rays act as background noise against the near-field light rays 8 generated at the tip end of nanotube 1. To avoid the influence of the background noise, the distance 745 between the tip end of tip 730 and the tip end of nanotube 1 is preferably larger than the size of the tip end of the tip, more preferably, they are distant from each other by, for example, several tens to several hundreds nm or more. Further, as shown in FIG. 31, by disposing a light shield plate 750 provided with a pinhole 750p at a position which is conjugate to the tip end of the nanotube 1 and which immediately precedes the photoelectric conversion element 340 (image forming position), only propagation light rays 757 converted from the near-field light rays 8 at the tip end of nanotube 1 can selectively be passed and propagation light rays converted from the near-field light rays at the tip end of tip 730 can be shielded.

According to the present embodiment, like the first embodiment, not only the AFM image and the near-field optical image can be captured simultaneously but also near-field light rays 8 of spot diameter 4 nm can constantly be generated stably between the gold nanoparticle 2b exposed to the lower end of nanotube 1 and the sample 10 and besides, by detecting near-field light rays 8 at an instant that the nanotube 1 is brought into contact with the sample 10 at a low contact force, that is, the gold nanoparticle 2b comes into contact with the sample 10, stable detection of the near-field light rays can be achieved. As a result, the resolution of the two-dimensional near-field optical image can be improved and the reproducibility of the image can be improved drastically.

(Modification of Cantilever 201)

A modified example of the cantilever 201 used as the light guide quarter will be described on the basis of FIG. 26. FIG. 26 illustrates the structure of a light guide quarter for a plasmon intensifying near-field probe in the present modification. The structure and function of cantilever 201, tip 730 and nanotube 1 are similar to those shown in FIG. 25.

In the present modification, by adjusting an angle of a ridge line 730w of triangular pyramid shaped tip 730 to the cantilever 201, the incident angle of excitation light rays 5a and 5b to the back surface 201s of cantilever 201 is made to be 0°, that is, vertical incidence can be set up. When the cantilever 201 and tip 730 are made of Si, a near infrared laser beam of, for example a wavelength of 830 nm is used for excitation light rays 5a and 5b which in turn are converged with the help of the NA (Numerical Aperture) of 0.2 and vertically irradiated on the back surface 201s of cantilever 201. The polarization direction 5p is P polarization and the converging angle 735 is about 23°. Incident excitation light rays are converged on the ridge line 730w of triangular pyramid tip 730. The converging angle 737 is about 6°. Preferably, the tip 730 is formed while the angle of ridge line 730w to the cantilever 201 is adjusted in advance so that the incident angle to the ridge line 730w may preferably be set to more than about 16° which is the critical angle. Coated on the surface of tip 730 are gold thin films 730f and 730r. In consideration of the efficiency of generation of plasmon, the film thickness of the gold thin film 730f along the ridge line 730w is about 50 nm and the thickness of two slant surfaces sandwiching the ridge line 730w is preferably thinner than the former thickness. With the excitation light rays of P polarization irradiated on the ridge line 730w, a TM (Transverse Magnetic) mode plasmon 740 is excited along the surface of the metal thin film 730f and it propagates towards the tip end of tip 730. The permissible range of resonance dip incident angle 738 for excitation of the plasmon is 2°~3° at the most and therefore, the range of converging angle 737 of excitation light rays is preferably about 6° which is twice the former angle mentioned as above. The excited TM mode plasmon 740 propagates from upper end to lower end along the surface of the nanotube 1 fixed to the tip end of tip 730 and by way of gold nanoparticles 2a, 2c and 2b filled in the interior of the nanotube as shown at dotted arrows 7a and 7b in FIG. 27. As shown in FIG. 27, since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light rays 8. Like the foregoing embodiment, cantilever 210 and tip 730 made of $Si_3N_4$ can be applicable.

The spot diameter of the near-field light rays 8 becomes 4 nm substantially equal to the size of gold nanoparticle 2b when the gold nanoparticle 2b approaches the sample 10 most closely. In other words, with this probe, an optical resolution of 4 nm can be obtained. In the present modification, the gold nanoparticle array is shown as the metal structure filled in the nanotube 1 but the invention is not limited thereto and similar effects can be attained even by filling a gold nanorod 702, for example, as shown in FIG. 28. The material of the nanorod may be another kind of metal and even with a silver nanorod, for example, a similar effect can be attained.

According to the present modification, not only the AFM image and the near-field optical image can be captured simultaneously but also near-field light rays 8 of spot diameter 4 nm can constantly be generated stably between the gold nanoparticle 2b exposed to the lower end of nanotube 1 and the sample 10 and besides, by detecting near-field light rays 8 at an instant that the nanotube 1 is brought into contact with the sample 10 at a low contact force, that is, the gold nanoparticle 2b comes into contact with the sample 10, stable detection of the near-field light rays can be achieved. As a result, the resolution of the two-dimensional near-field optical image can be improved and the reproducibility of the image can be improved drastically.

(Modification of Plasmon Intensifying Near-Field Probe)

A modified example of the plasmon intensifying near-field probe will be described on the basis of FIGS. 29 and 32. FIG. 29 illustrates the structure of a plasmon intensifying near-field probe in the present modification. Like the first embodiment and its modifications, the nanotube is a multiwall carbon nanotube 1 or a metal nanotube 1, having the lower end sharpened conically. The structure and function of cantilever 201 and tip 730 are similar to those shown in FIG. 25 or 26.

In the present modification, the upper end of a nanotube 1 is not filled with a gold nanoparticle but is filled with a fluorescent particle 770 of either metal carbide such as V, Y, Ta, Sb or the like exhibiting photoluminescence or electroluminescence or a ZnS fluorescent material, a CaS fluorescent material or CdSe (core)/ZnS (outer shell) and the lower end is filled with the gold nanoparticle 2b like the other embodiments, as shown in FIG. 29. Like FIG. 26 or 27, the gold nanoparticle or nanorod may be filled midway through the nanotube 1.

FIG. 32 illustrates the construction of a scanning probe microscope carrying the present probe. The present scanning probe microscope has the basic construction and function similar to those of the scanning probe microscope in the embodiment shown in FIG. 9 but differs in that that a wavelength selection filter 755 having a transmission band for (a fluorescent wavelength at which the fluorescent particle 770 fluoresces)±10 nm is arranged immediately before the photoelectric conversion element 340 such as photodiode or photomultiplier tube for detection of near-field light rays. More particularly, as shown in FIG. 25, a TM mode plasmon 740 excited by excitation light rays 5a and 5b propagates toward the tip end of tip 730. The TM mode plasmon 740 excites the fluorescent particle 770 filled in the upper end of nanotube 1 shown in FIG. 29 to generate fluorescence of a wavelength different from that of the excitation light rays 5a and 5b, thus inducing a micro-spotlight of the same wavelength as that of the fluorescence. The micro-spotlight excites a surface plasmon in the nanotube 1 and the surface plasmon propagates through the nanotube 1 from upper end to lower end as shown at dotted arrows 780a and 780b. Since the lower end of nanotube 1 is sharpened conically, the intensity of electric field is strengthened locally and an intensive local plasmon is excited in the gold nanoparticle 2b at the lower end of nanotube 1. The local plasmon interacts with the surface structure of the sample 10 to generate an intensive resonance phenomenon, causing micro-near-field light rays 790 of the same wavelength as that of the fluorescence.

The spot diameter of the near-field light rays 790 becomes 4 nm substantially equal to the size of gold nanoparticle 2b when the gold nanoparticle 2b approaches the sample 10 most closely. In other words, with this probe, an optical resolution of 4 nm can be obtained. Reflection rays of near-field light rays 790 turn into propagation light rays 9a and 9b which in turn are converged by objective lens 320 to parallel light rays 90a and 90b. The parallel rays 90a and 90b transmit through the ring band transmission region 316a of beam splitter 315, transmitted light propagates through the image forming lens 330 and only a fluorescent wavelength component 760 is extracted by the wavelength selection filter 755, the extracted component being converted photoelectrically by the photoelectric conversion element 340 such as photodiode or photomultiplier tube. The ensuing procedures are similar to those in the scanning probe microscope in the embodiment shown in FIG. 9.

To add, in the present modification, the fluorescent particle 770 is used but this is not limitative and for example, by using a non-linear optical crystal, near-field light rays having a wavelength half the wavelength of the incident light can be generated.

According to the present modification, not only the AFM image and the near-field optical image can be captured simultaneously but also near-field light rays 790 of spot diameter 4 nm can constantly be generated stably between the gold nanoparticle 2b at the lower end of nanotube 1 and the sample 10 and besides, by detecting near-field light rays 790 at an instant that the nanotube 1 is brought into contact with the sample 10 at a low contact force, that is, the gold nanoparticle 2b comes into contact with the sample 10, stable detection of the near-field light rays can be achieved. As a result, the resolution of the two-dimensional near-field optical image can be improved and the reproducibility of the image can be improved drastically. Further, according to the present embodiment, near-field light rays generated at the tip end of tip 730 by the TM mode plasmon 740 failing to couple to the nanotube 1 have a wavelength equal to that of excitation light rays 5a and 5b in FIG. 25 whereas near-field light rays 790 generated at the lower end of nanotube 1 have a different fluorescent wavelength. In other words, the wavelength of the near-field light rays generated at the tip end of tip 730 and impersonating background noise can be separated and only the near-field light rays 790 generated at the lower end of nanotube 1 can be detected, thereby ensuring that the near-field optical image can be obtained at a high S/N ratio. Similarly, scattering rays and background noise generated by the laser beam rays 5a and 5b emitted from the solid laser 300 midway through the optical path or in the nanotube 1 itself can be reduced to a great extent and so a near-field ray image at high S/N ratio can be obtained.

While the invention made by the present inventors has been described specifically on the basis of the embodiments, the present invention is in no way limited to the foregoing embodiments and can obviously be changed, altered and modified in various ways without departing from the gist of the invention.

INDUSTRIAL APPLICABILITY

As has been set forth so far, according to the present invention, a scanning probe microscope having an optical resolution of nanometer order can be realized in addition to the AFM. Consequently, physical properties such as stress distribution and impurity distribution of a semiconductor sample can be measured and beside, optical information and topographic information contributing to classifying of foreign matters and defects can be measured, improving the foreign matter/defect classification performance. Further, by feeding the measurement results back to the semiconductor device production process condition, a semiconductor device of high reliability can be produced at a high yield.

BRIEF DESCRIPTION OF THE DRAWINGS

FIG. 16 is a schematic diagram showing combinations of data of the individual light source wavelengths with various materials and individual reflection light intensities.

Figure 1:
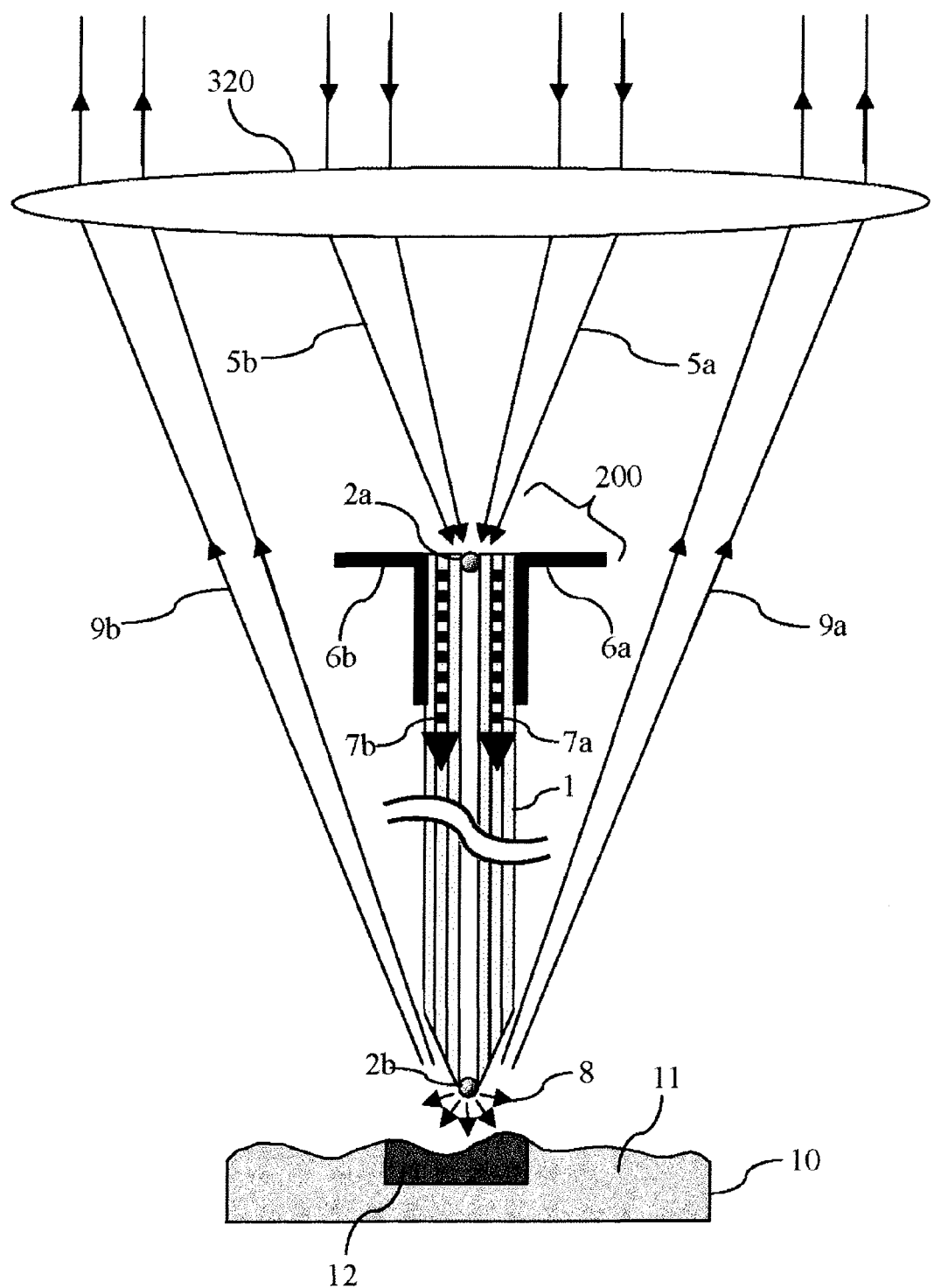
FIG. 1 is a frontal sectional diagram of a plasmon intensifying near-field probe in embodiment 1.
Figure 2:
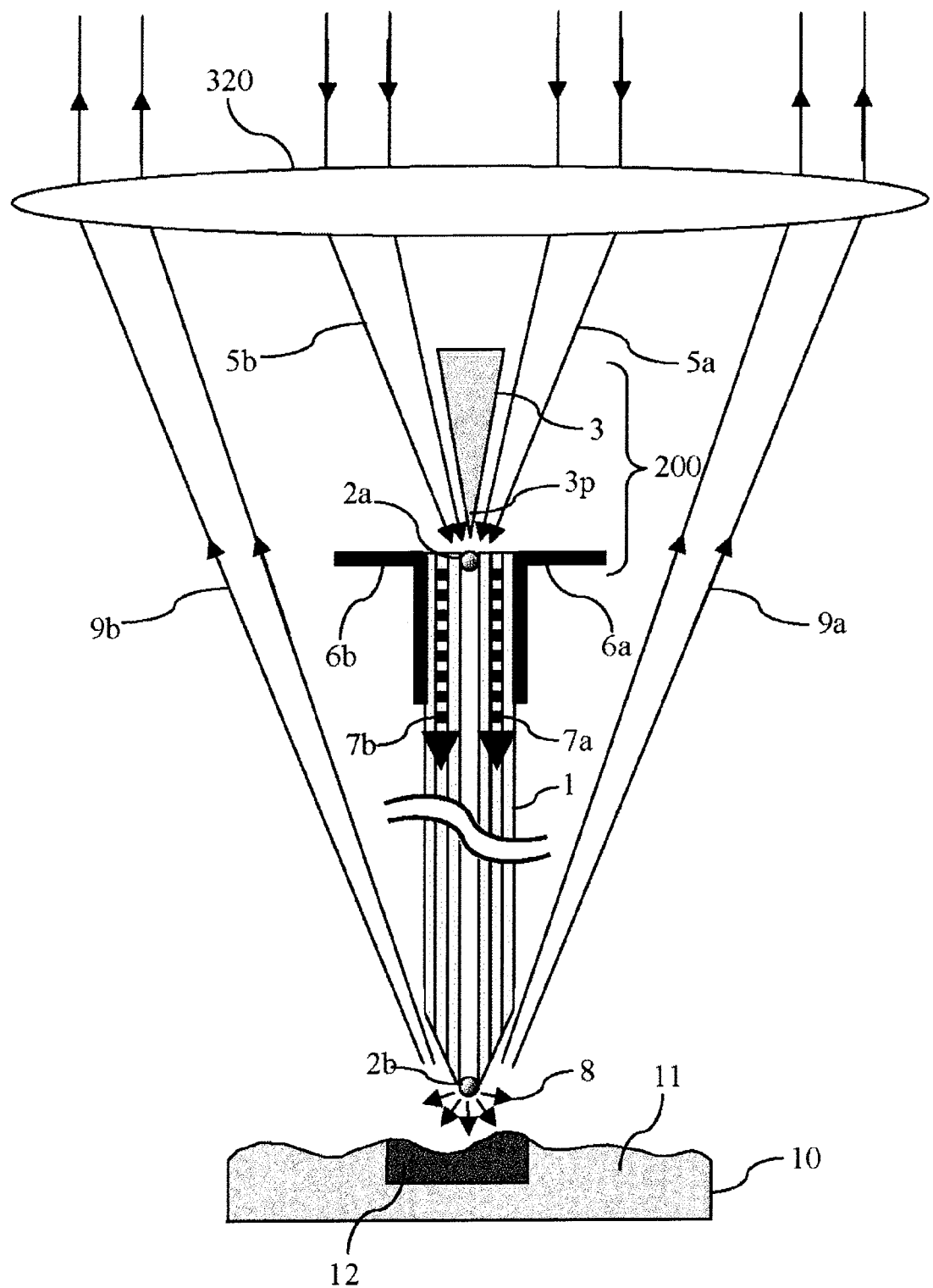
FIG. 2 is a frontal sectional diagram of a probe in modification 1 of a plasmon intensifying near-field probe light guide quarter 200 in embodiment 1.
Figure 3:
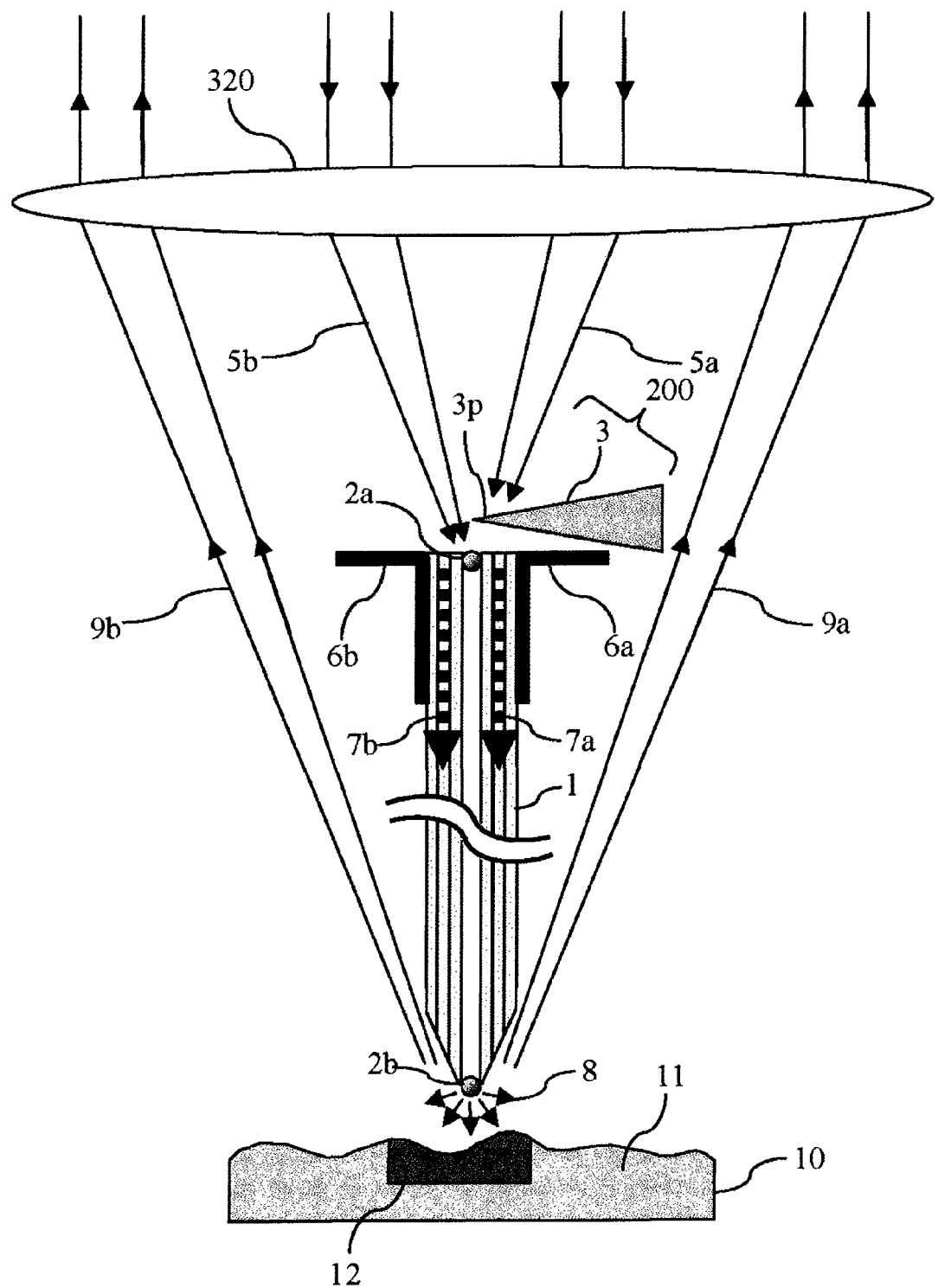
FIG. 3 is a frontal sectional diagram of a probe in modification 2 of a plasmon intensifying near-field probe light guide quarter 200 in embodiment 1.
Figure 4:
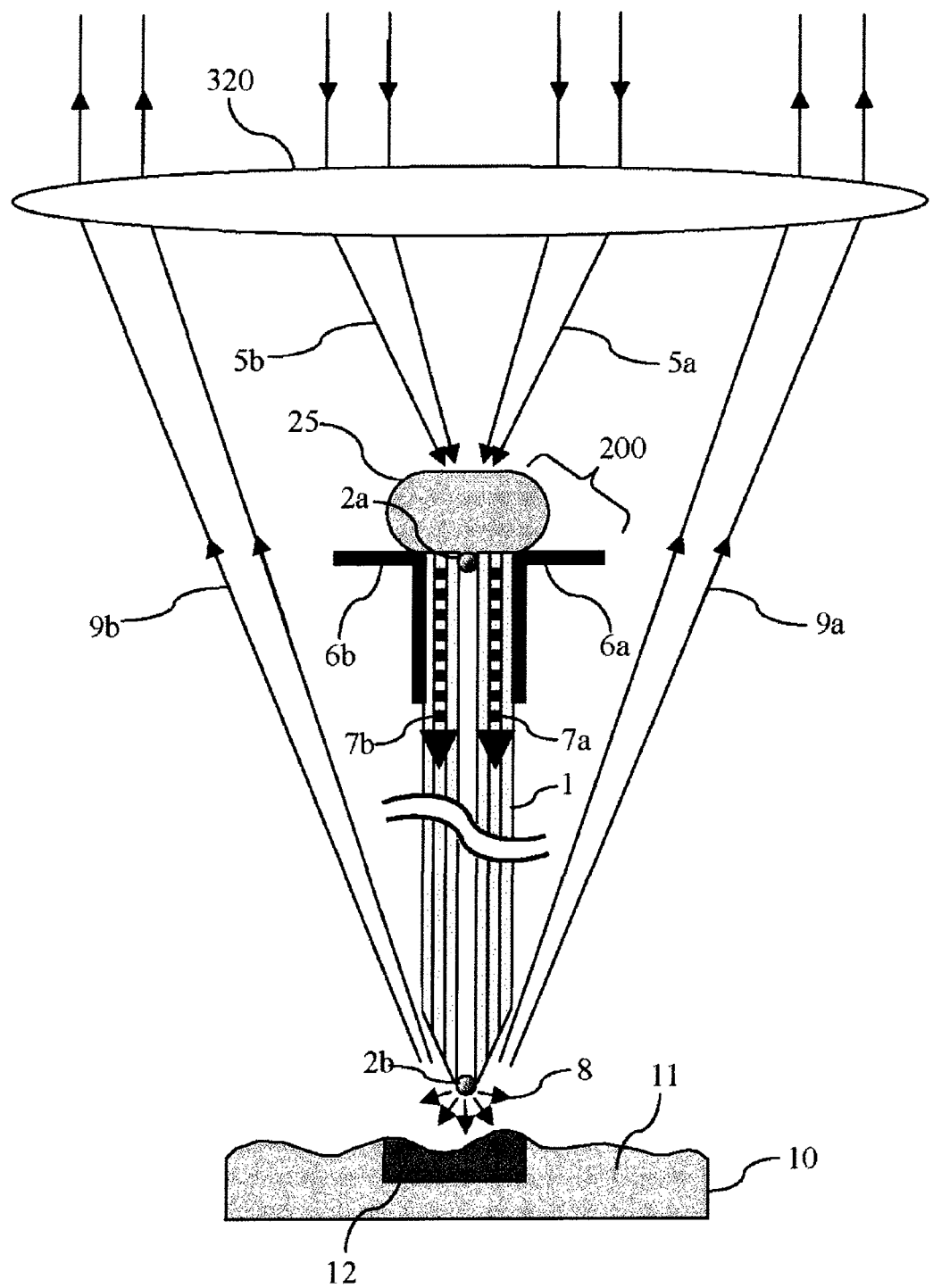
FIG. 4 is a frontal sectional diagram of a plasmon intensifying near-field probe in embodiment 2.
Figure 5:
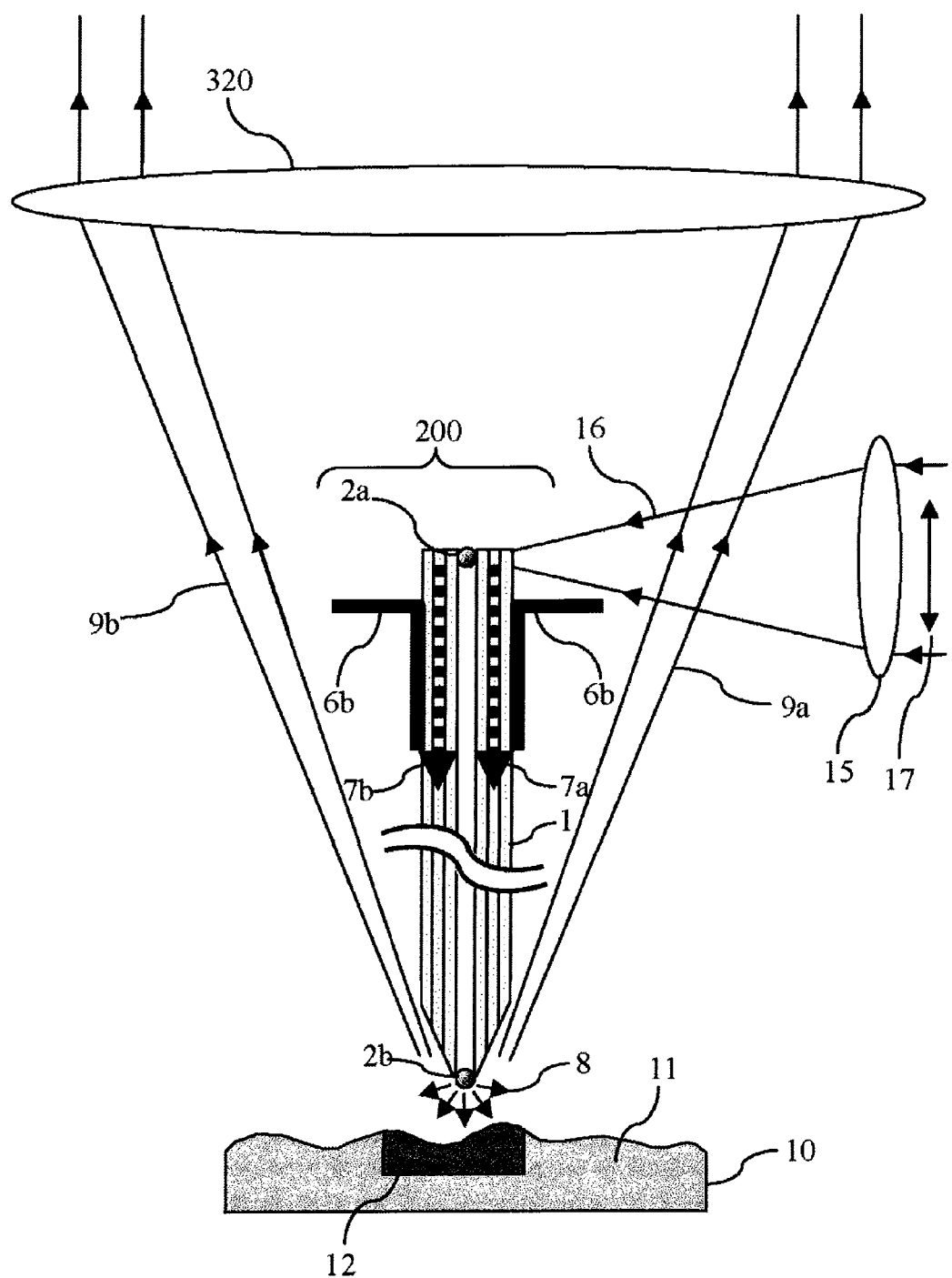
FIG. 5 is a frontal sectional diagram of a plasmon intensifying near-field probe in embodiment 3.
Figure 6:
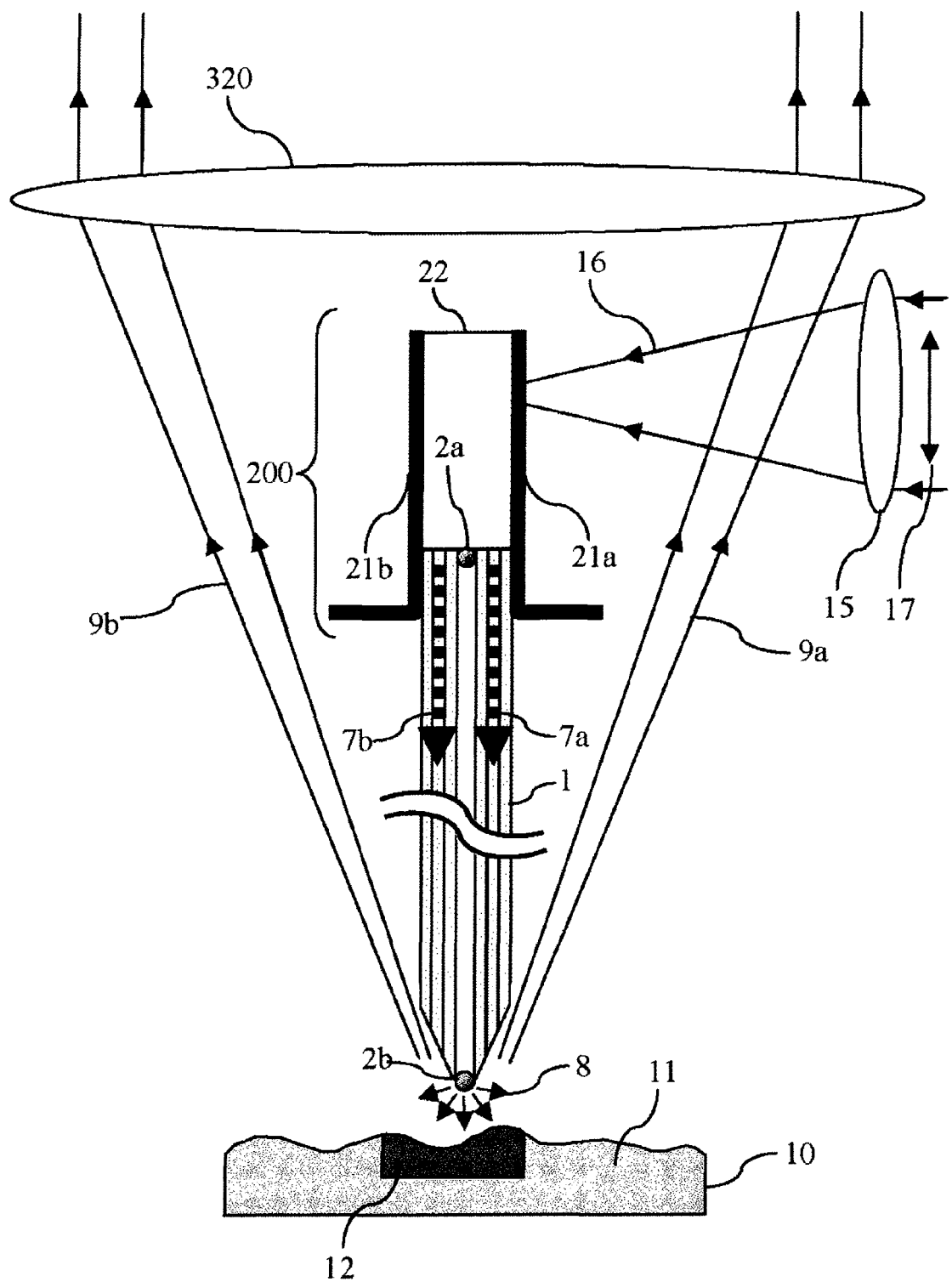
FIG. 6 is a frontal sectional diagram of a probe in a modification of a plasmon intensifying near-field probe light guide quarter 200 in embodiment 3.
Figure 7:
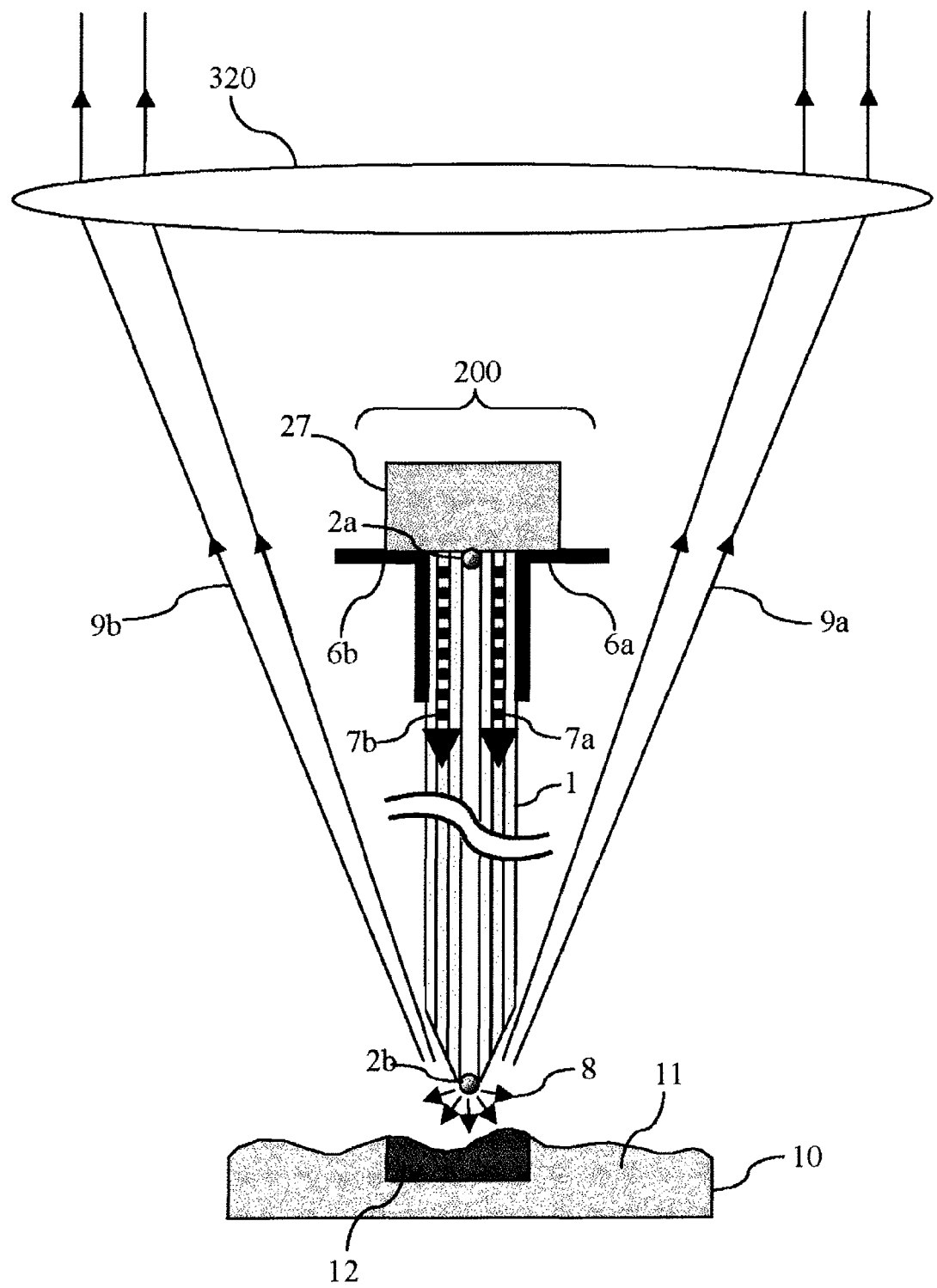
FIG. 7 is a frontal sectional diagram of a plasmon intensifying near-field probe in embodiment 4.
Figure 8:
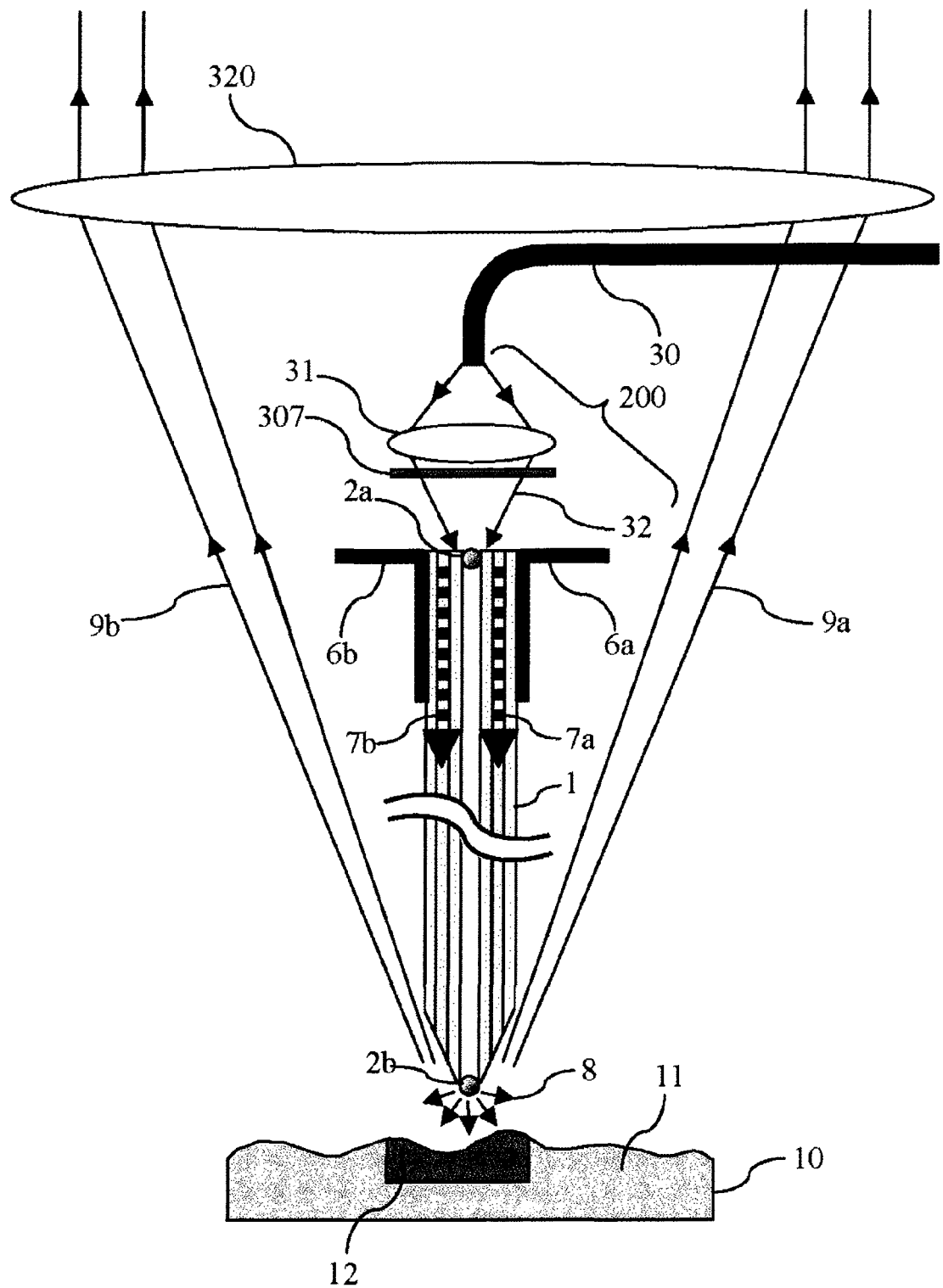
FIG. 8 is a frontal sectional diagram of a plasmon intensifying near-field probe in embodiment 5.
Figure 9:
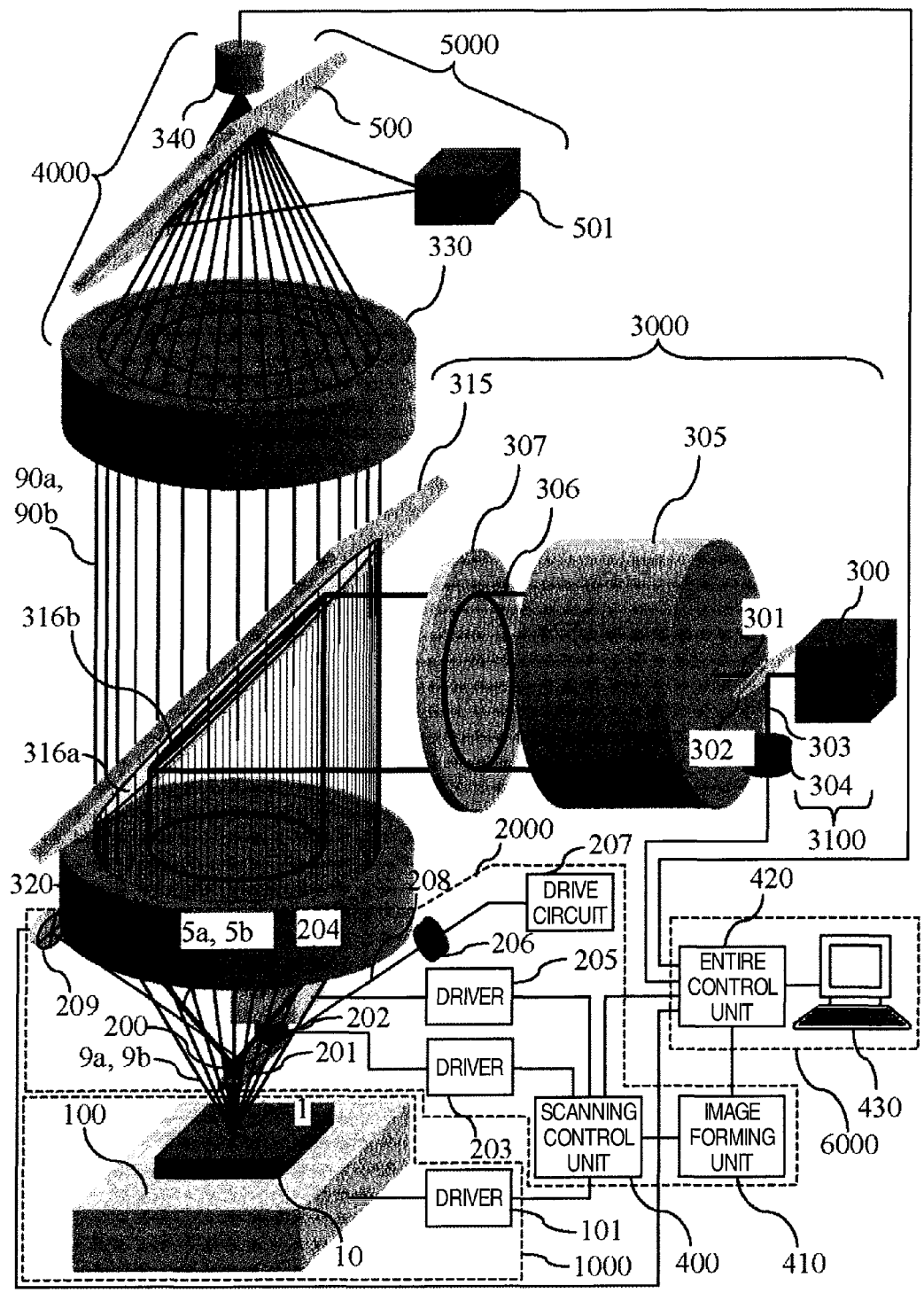
FIG. 9 is a block diagram showing schematic construction of a scanning probe microscope in embodiment 1.
Figure 10:
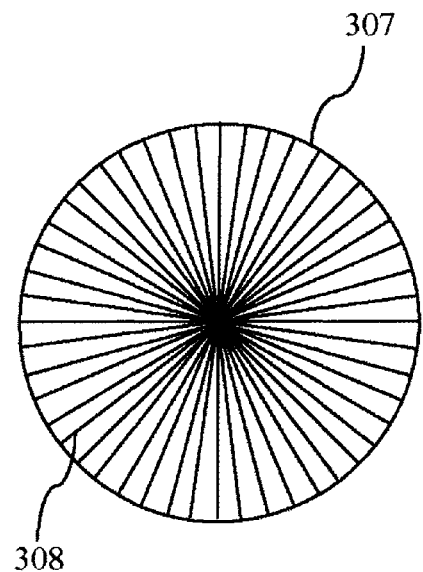
FIG. 10 is a schematic diagram showing polarization axes of a polarization plate.
Figure 11:
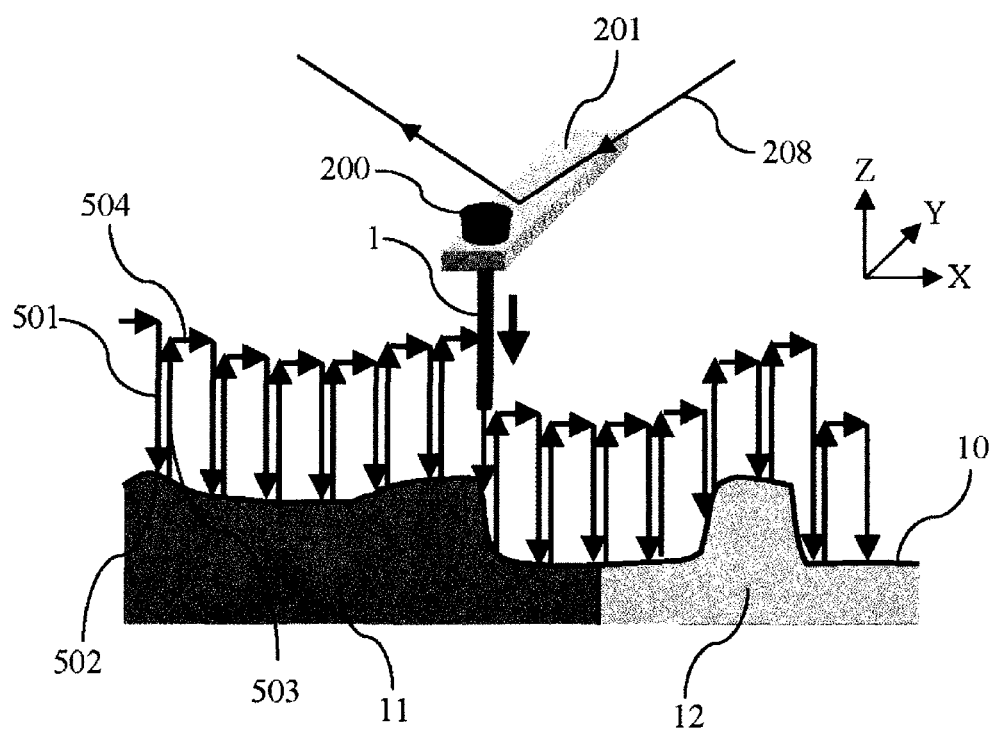
FIG. 11 shows a sample section diagram and a perspective view diagram of a cantilever for showing step-in scanning of a nanotube.
Figure 12:
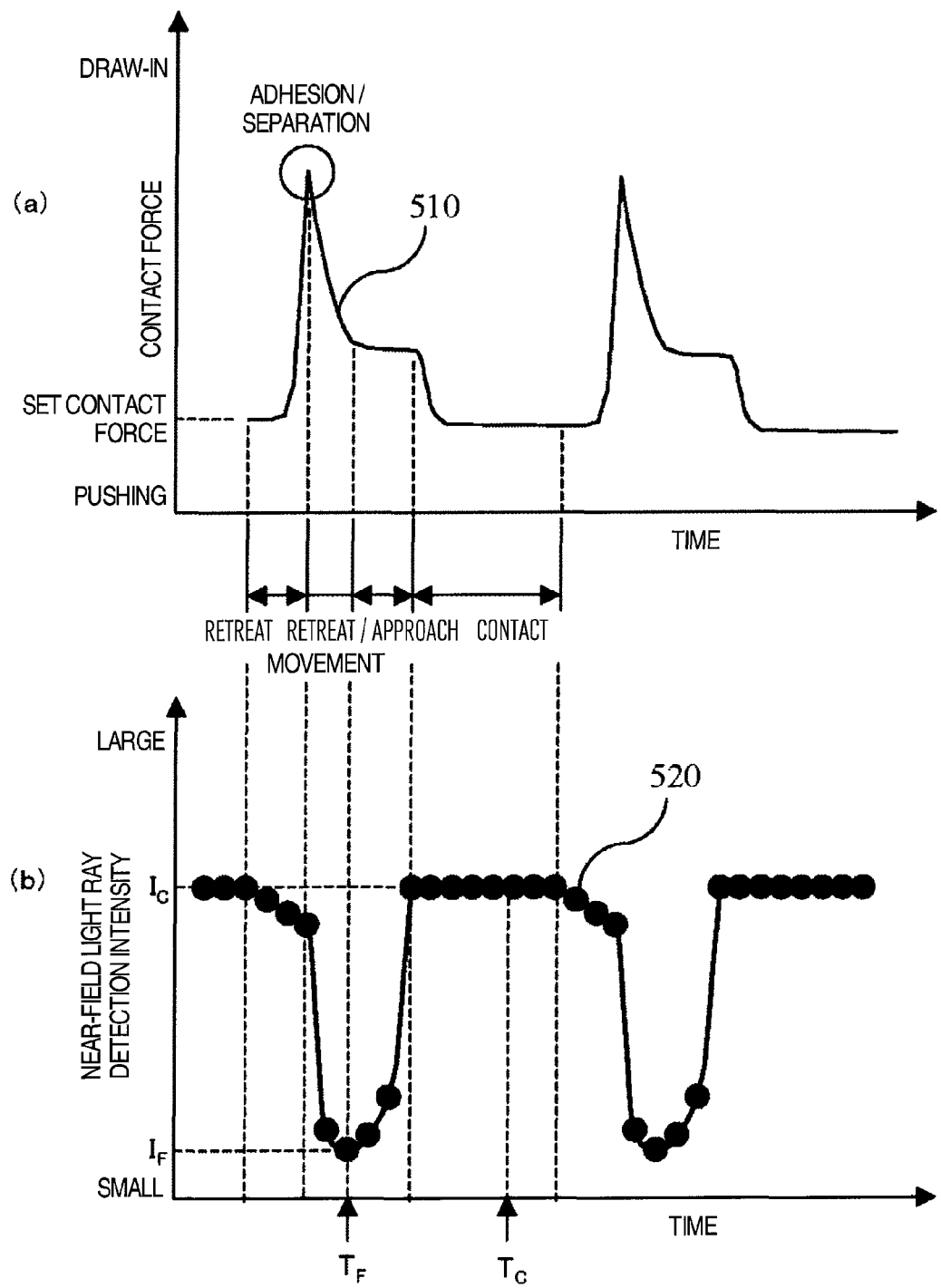
FIG. 12 shows graphs showing the relation between inter-nanotube/sample contact force and timings for measurement of near-field light rays.
Figure 13:
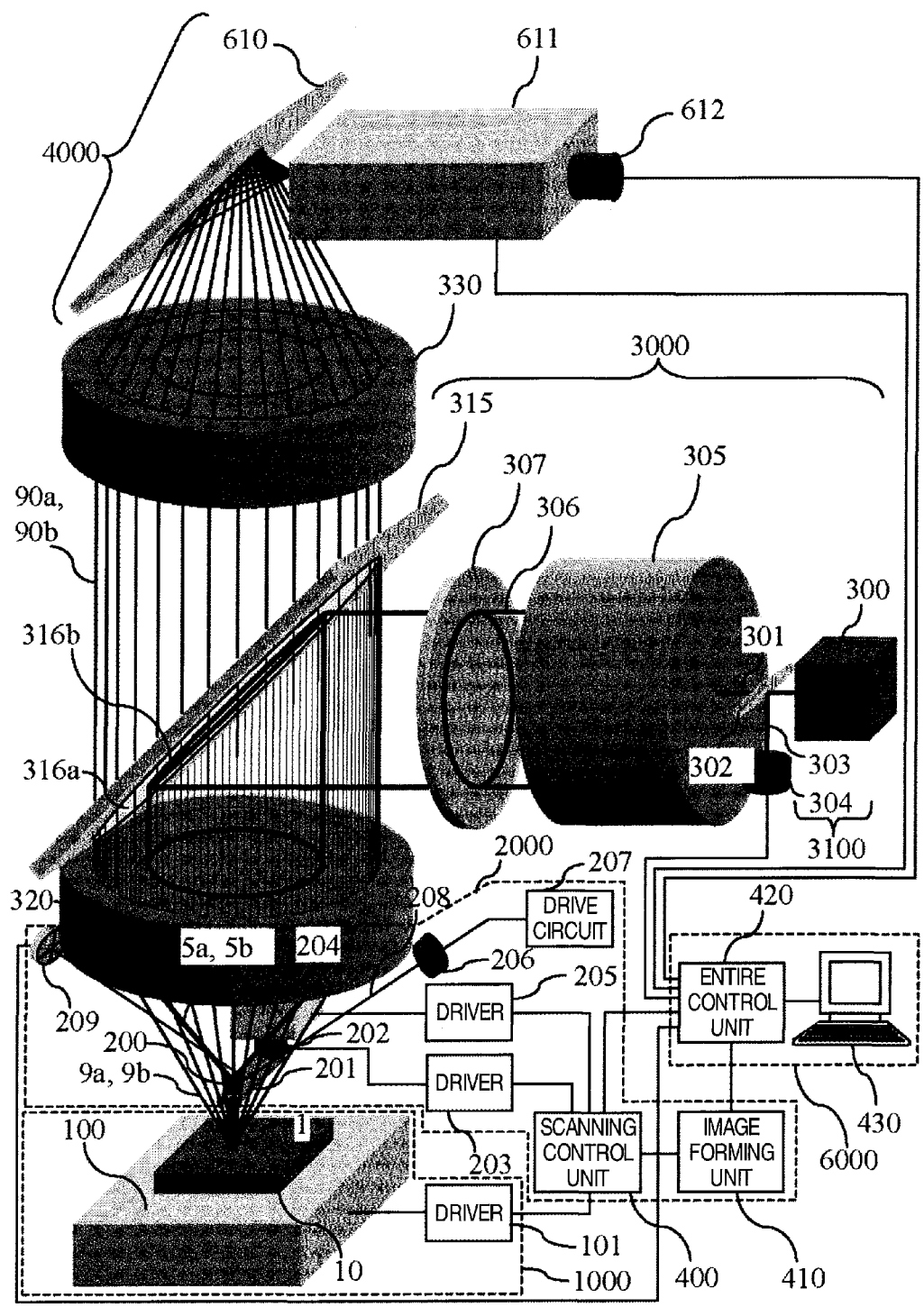
FIG. 13 is a block diagram showing schematic construction of a scanning probe microscope in modification 1 of a detection optical system 4000 in embodiment 1.
Figure 14:
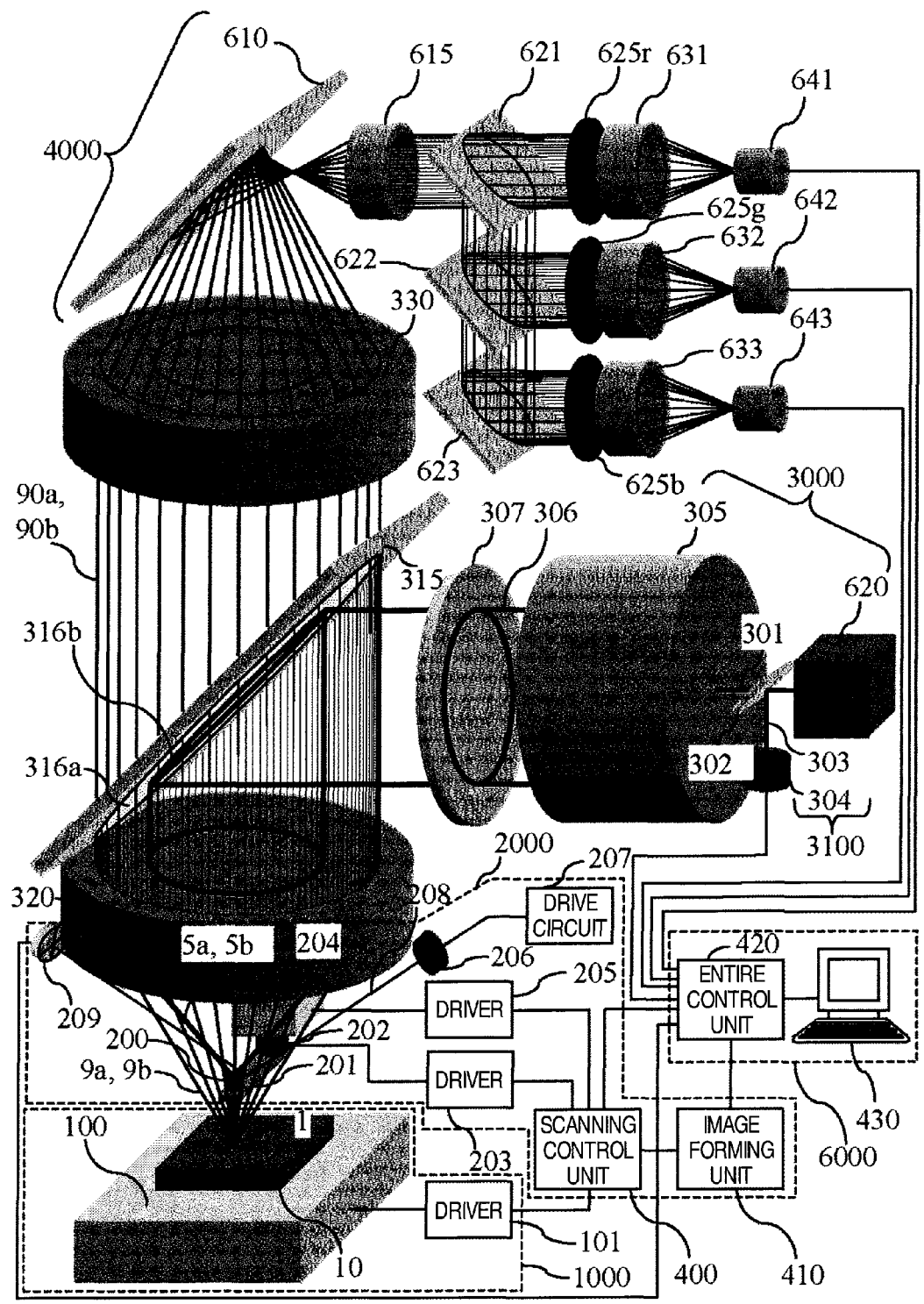
FIG. 14 is a block diagram showing schematic construction of a scanning probe microscope in modification 2 of a detection optical system 4000 in embodiment 1.
Figure 15:
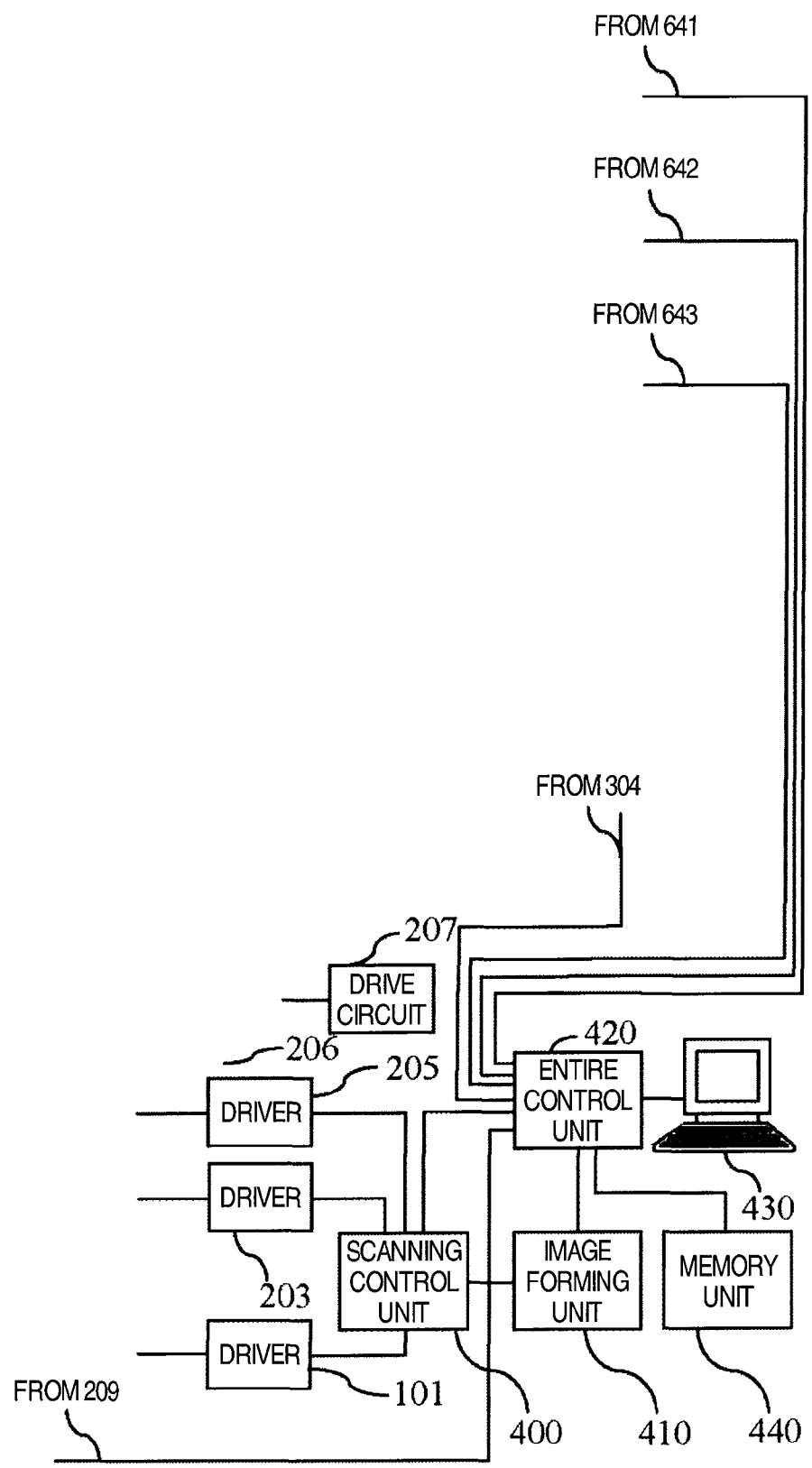
FIG. 15 is a block diagram showing schematic construction of a scanning probe microscope in modification 1 of a measurement unit 2000 in embodiment 1.
Figure 17:
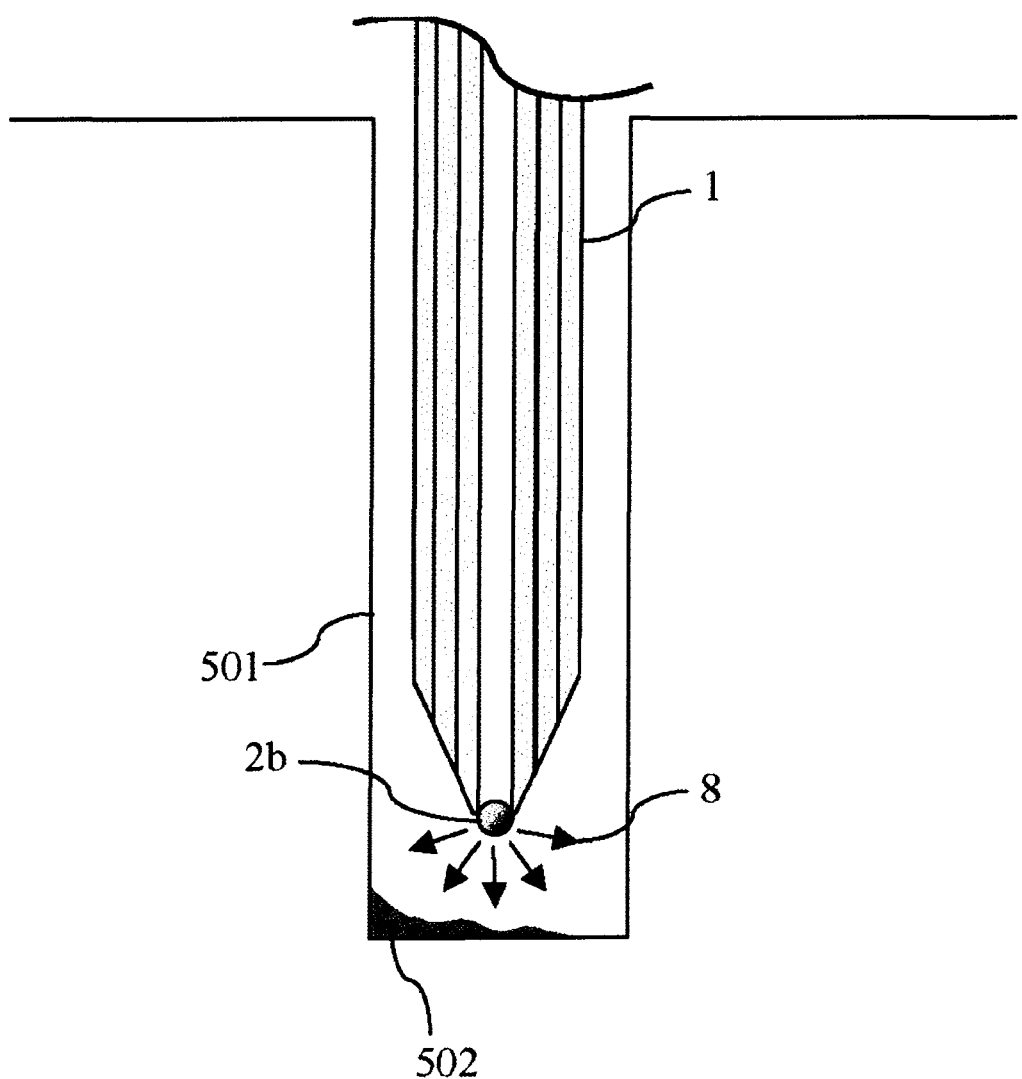
FIG. 17 shows a section of a deep hole and a frontal sectional diagram of a plasmon intensifying near-field probe to show an example in which the scanning probe microscope in modification 1 of a measurement unit 2000 in embodiment 1 is applied to detection of a residual film at the lower end of a deep hole such as contact hole.
Figure 18:
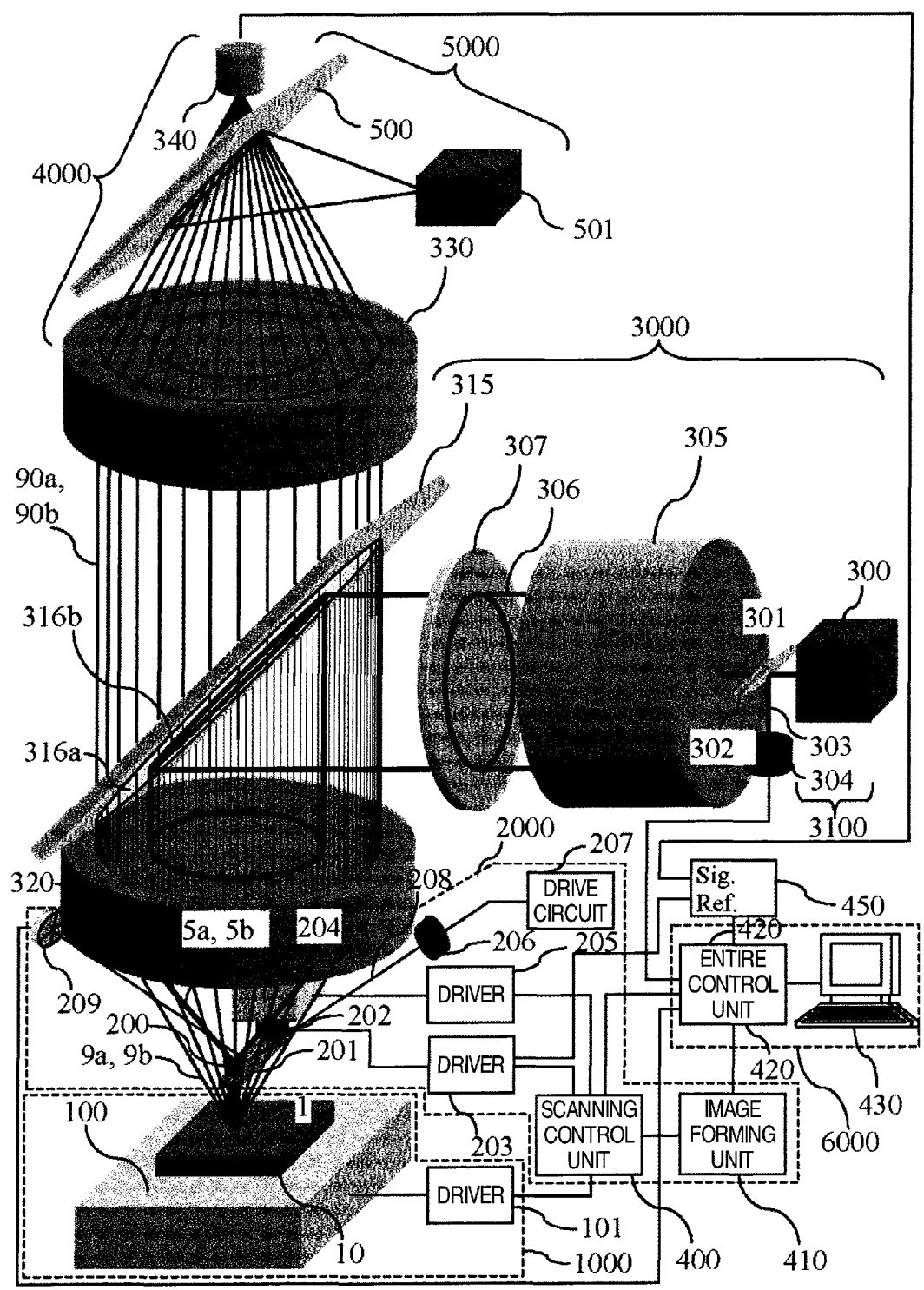
FIG. 18 is a block diagram showing schematic construction of a scanning probe microscope in modification 2 of a measurement unit 2000 in embodiment 1.
Figure 19:
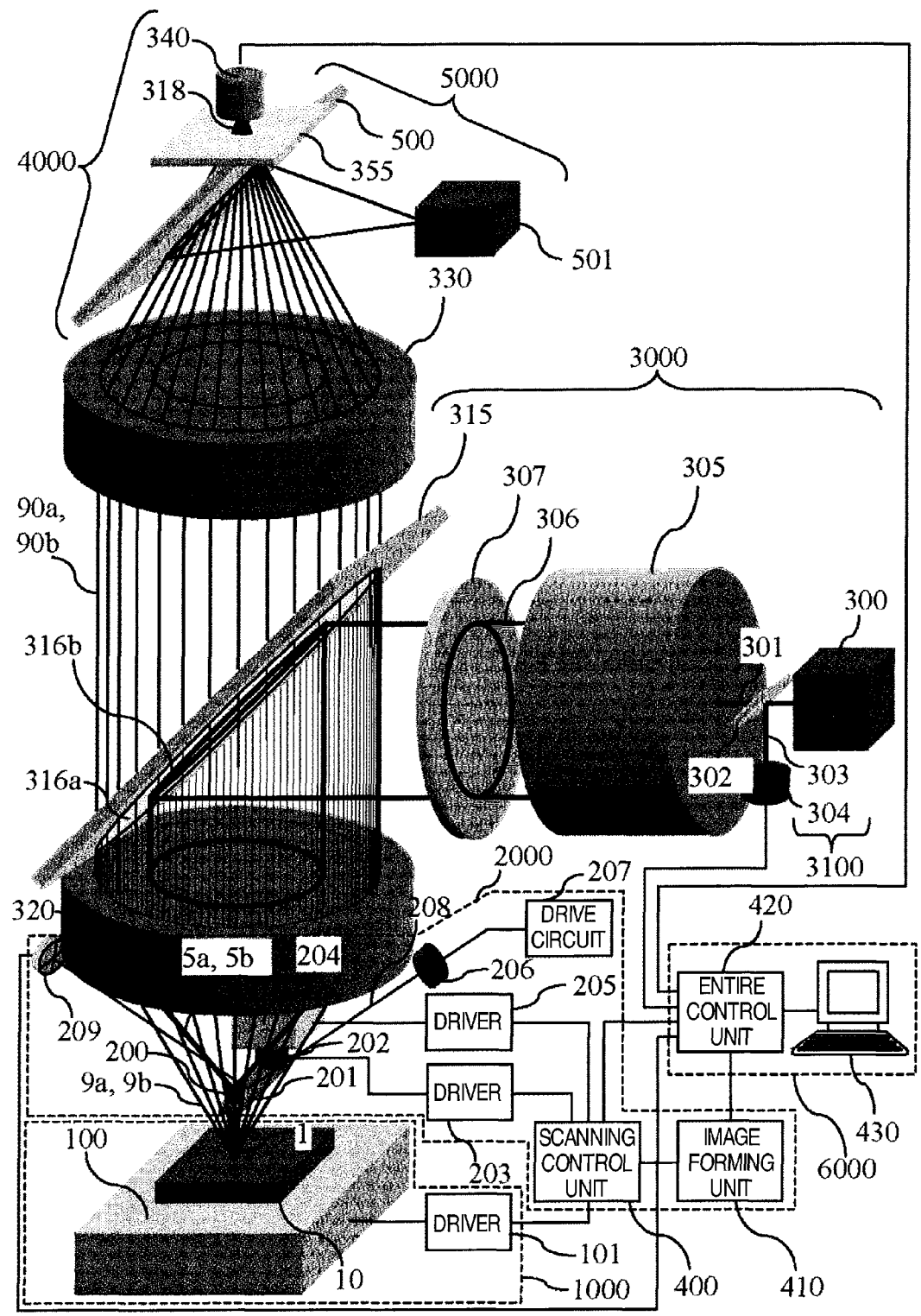
FIG. 19 is a block diagram showing schematic construction of a scanning probe microscope in embodiment 2.
Figure 20:
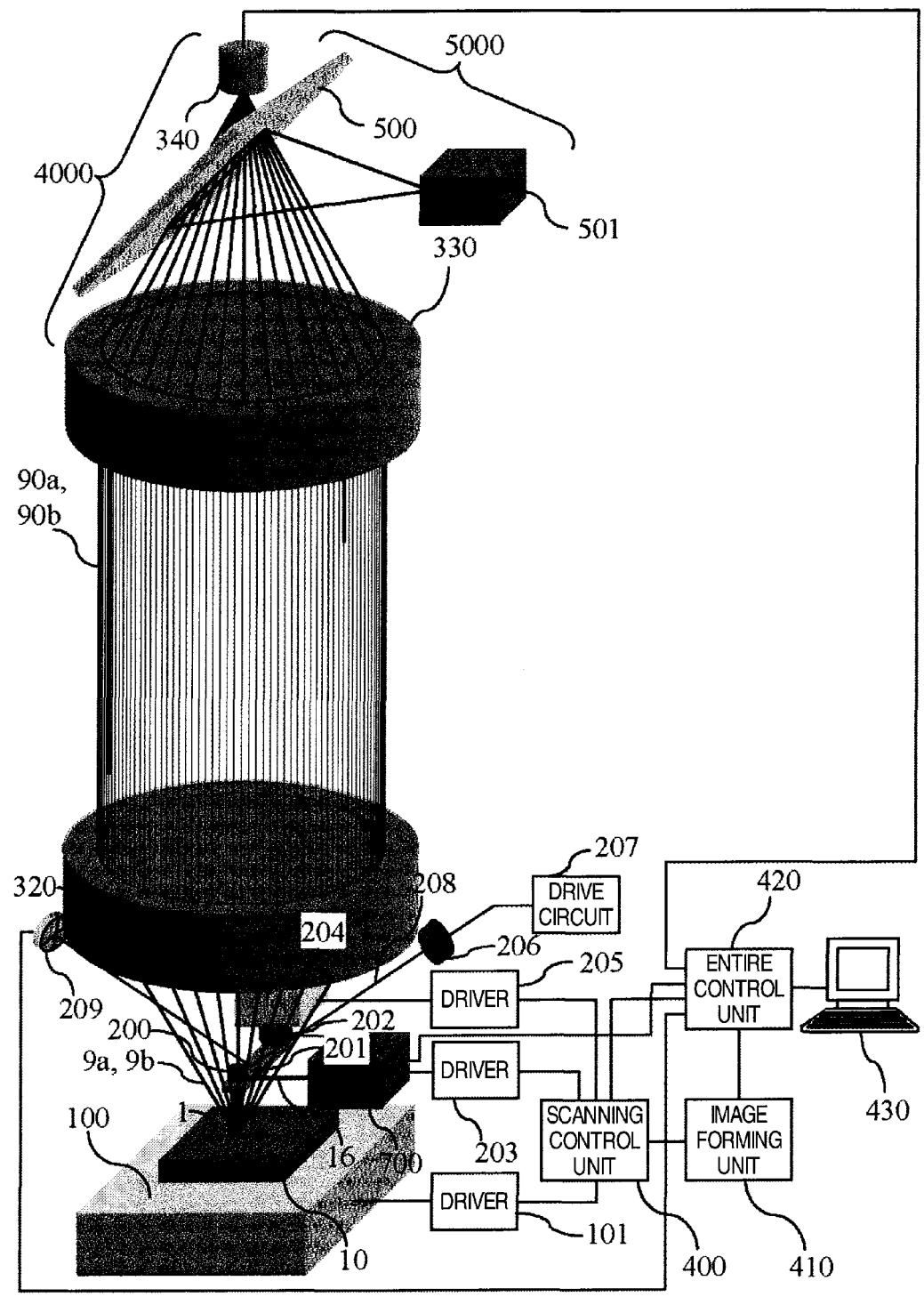
FIG. 20 is a block diagram showing schematic construction of a scanning probe microscope in embodiment 3.
Figure 21:
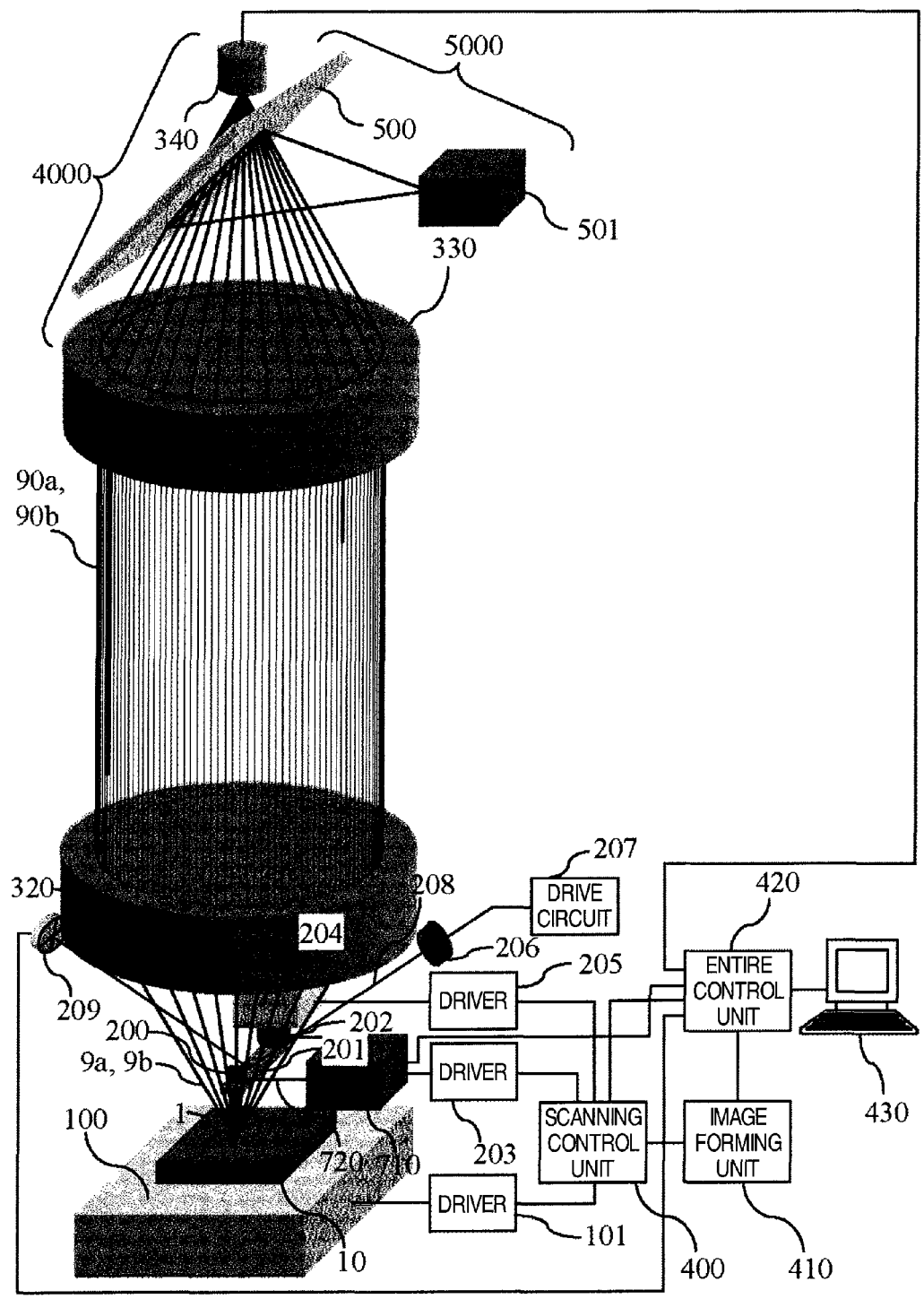
FIG. 21 is a block diagram showing schematic construction of a scanning probe microscope in embodiment 4
Figure 22:
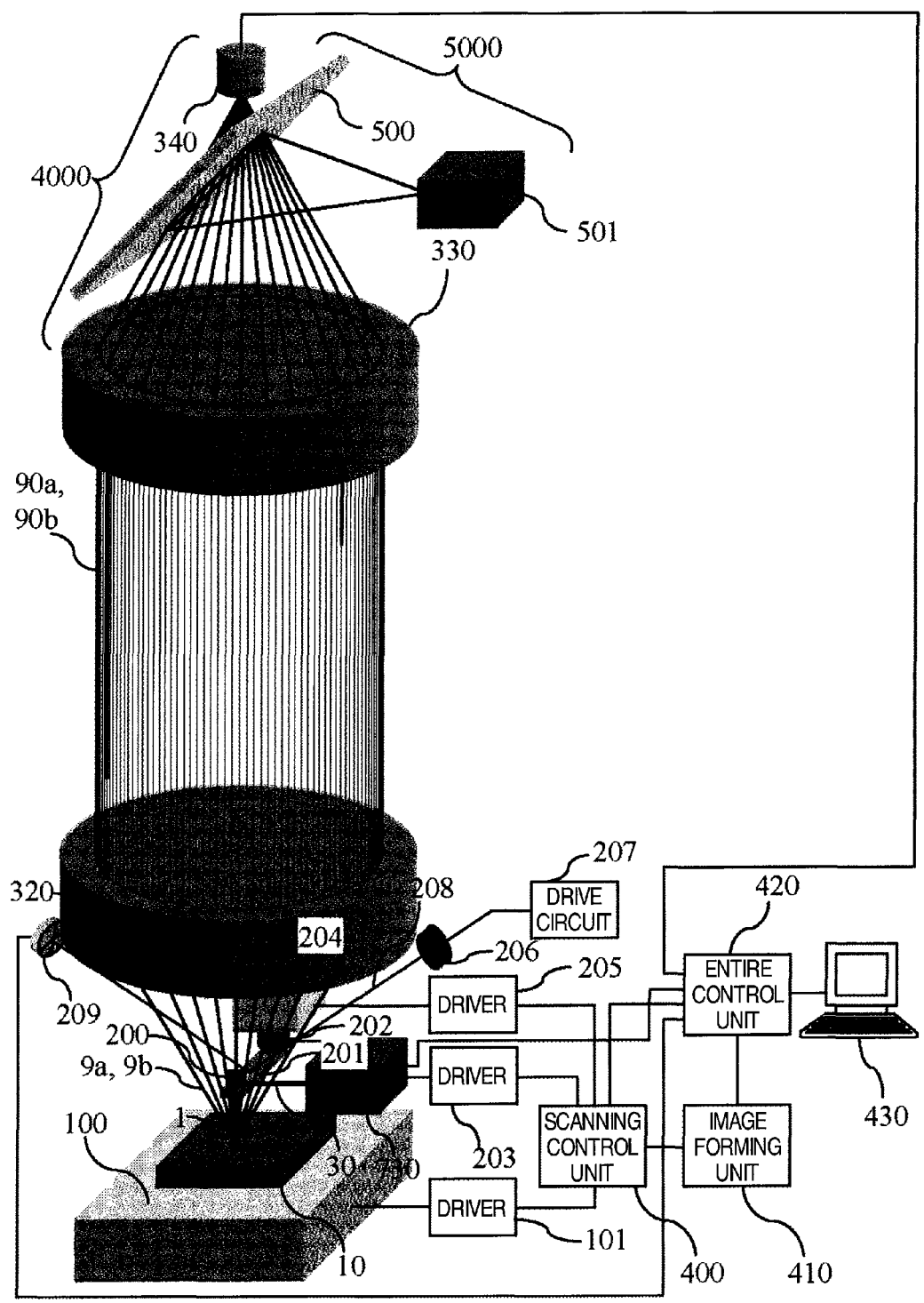
FIG. 22 is a block diagram showing schematic construction of a scanning probe microscope in embodiment 5
Figure 23:
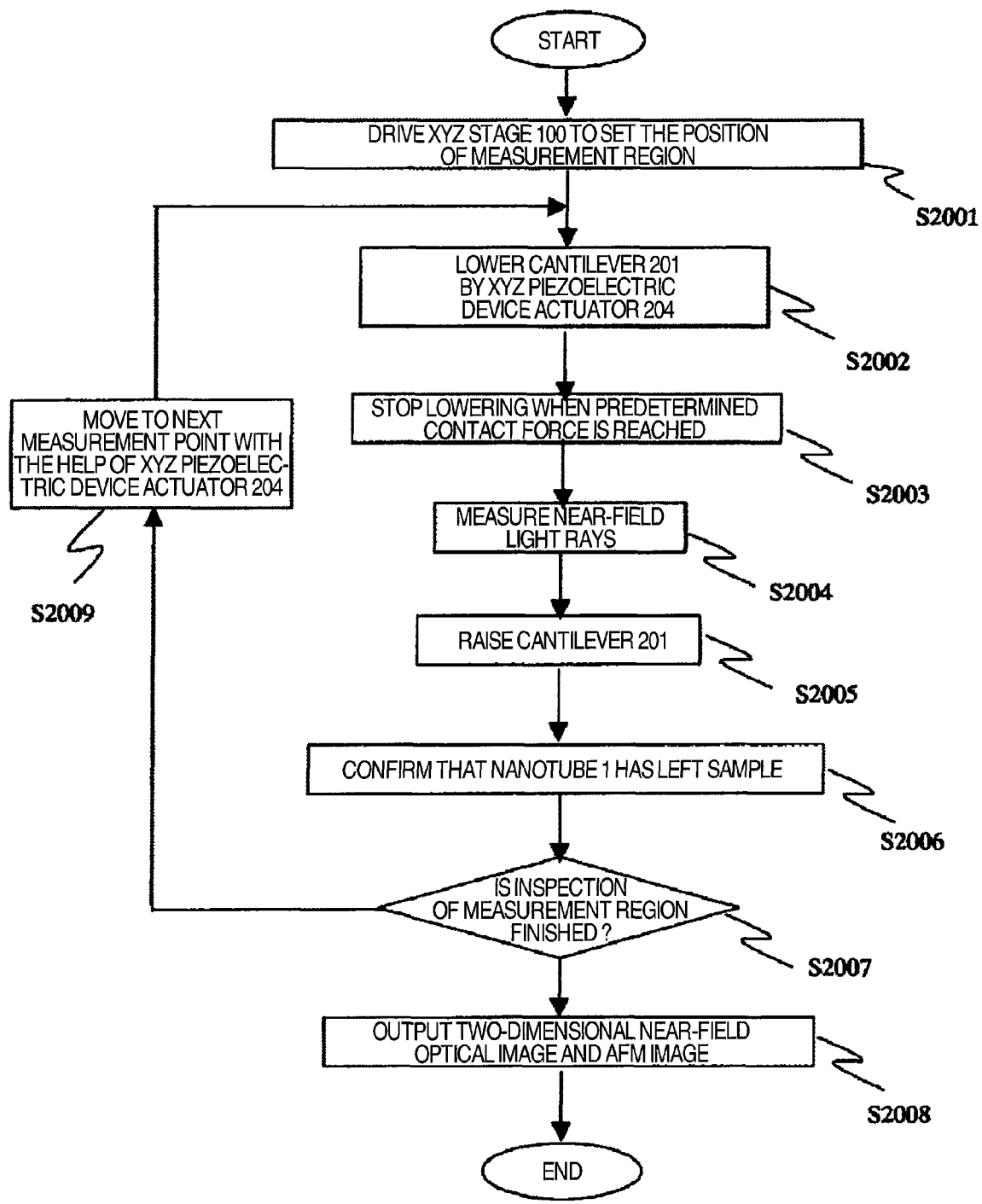
FIG. 23 is a flowchart showing procedures for measuring a sample surface in embodiments 1 through 5.
Figure 24:
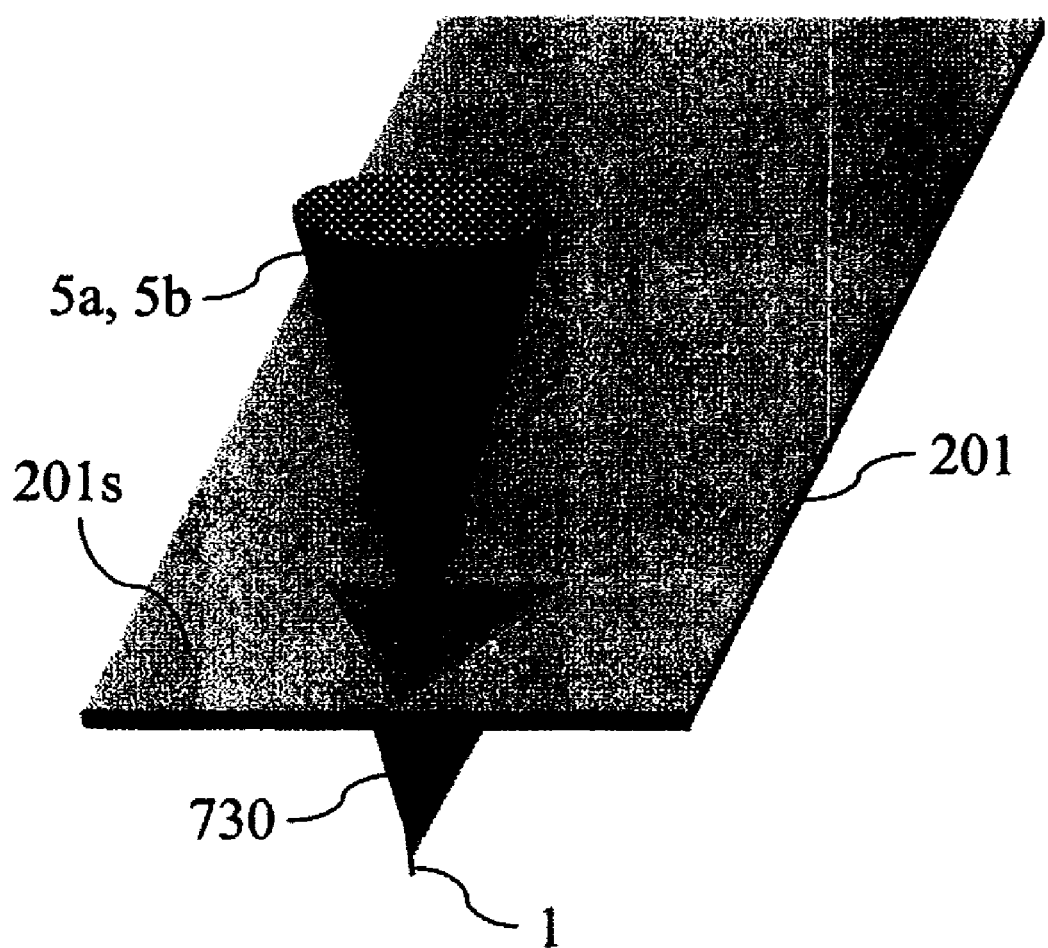
FIG. 24 is a perspective view diagram of a plasmon intensifying near-field probe light guide quarter in embodiment 6.
Figure 25:
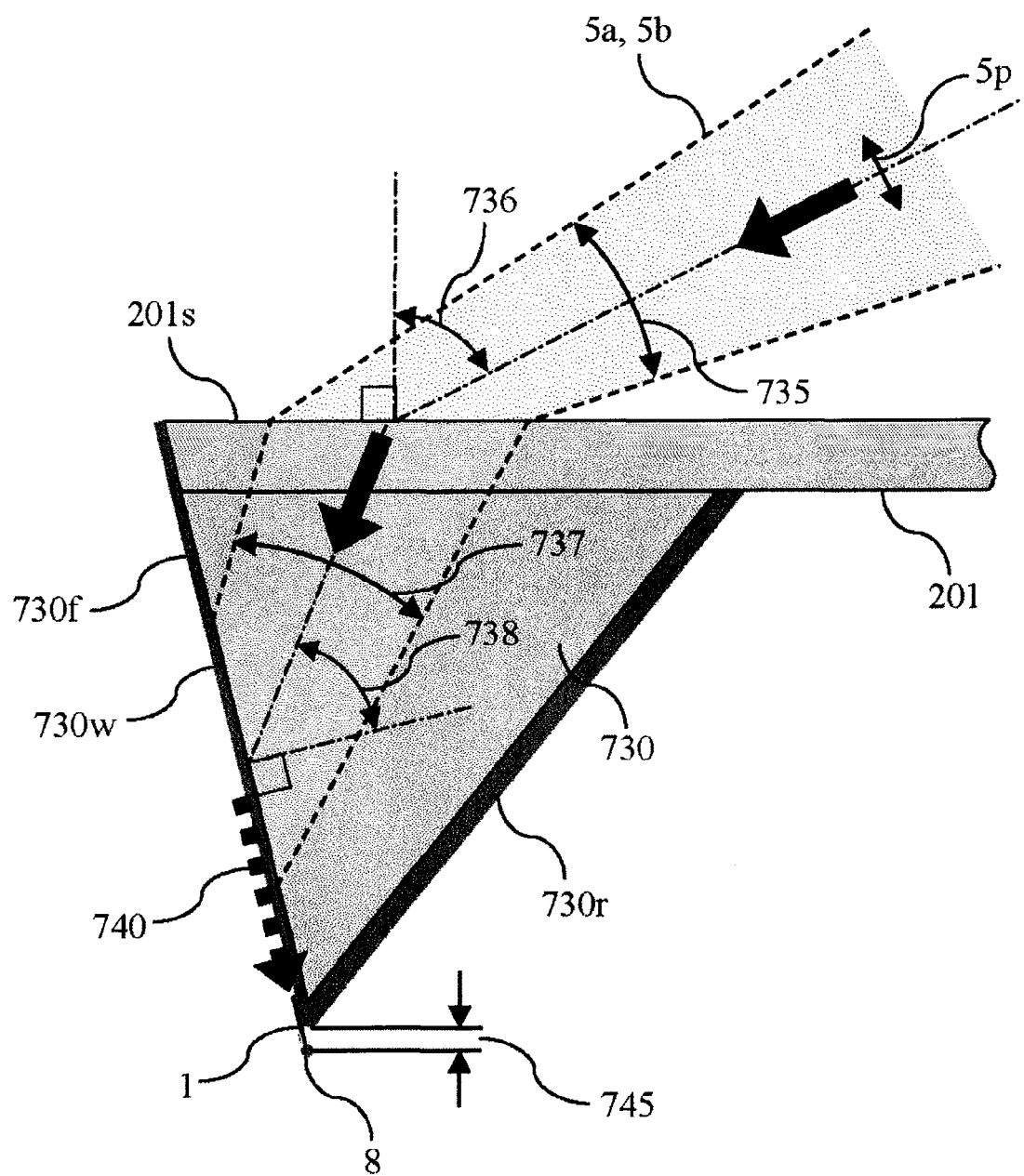
FIG. 25 is a side sectional diagram of a plasmon intensifying near-field probe light guide quarter cantilever 201 in embodiment 6.
Figure 26:
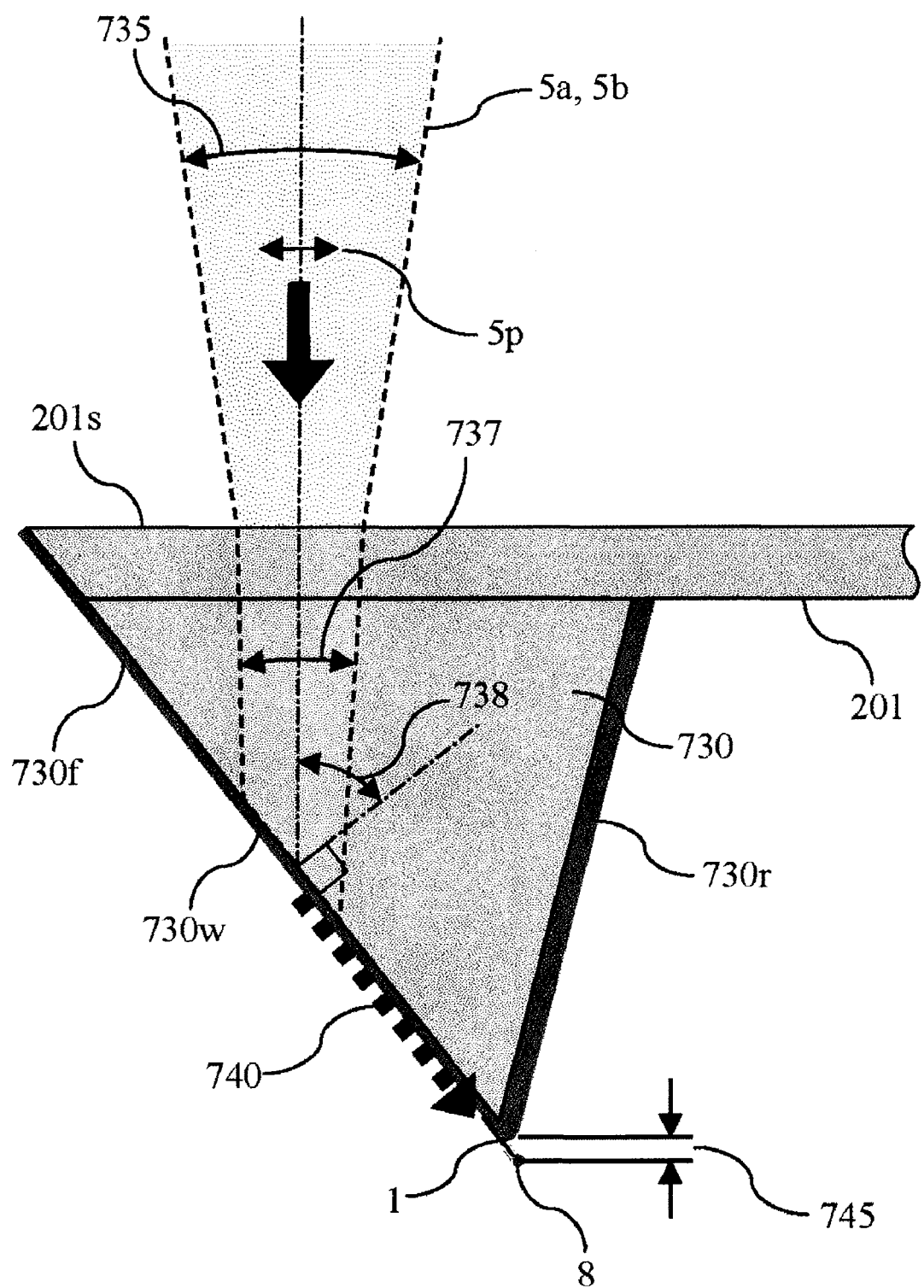
FIG. 26 is a side sectional diagram of a modification of a plasmon intensifying near-field probe light guide quarter cantilever 201 in embodiment 6.
Figure 27:
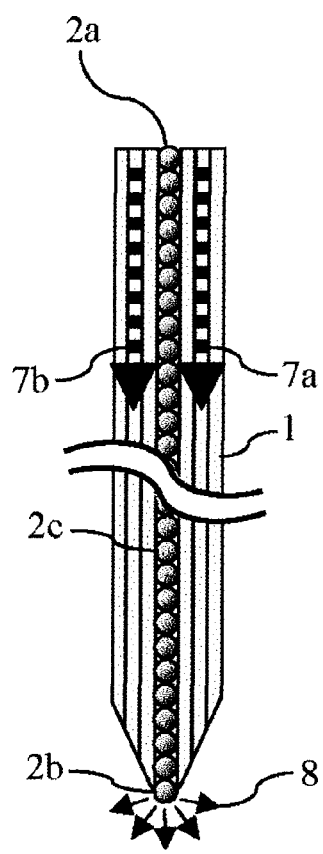
FIG. 27 is a frontal sectional diagram of a gold nanoparticle filled plasmon intensifying near-field probe in embodiment 6.
Figure 28:
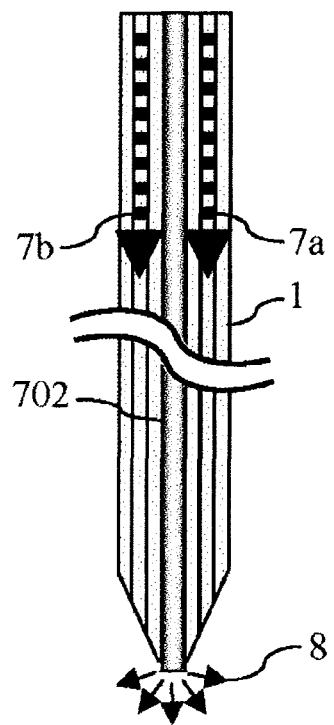
FIG. 28 is a frontal sectional diagram of a gold nanorod filled plasmon intensifying near-field probe in embodiment 6.
Figure 29:
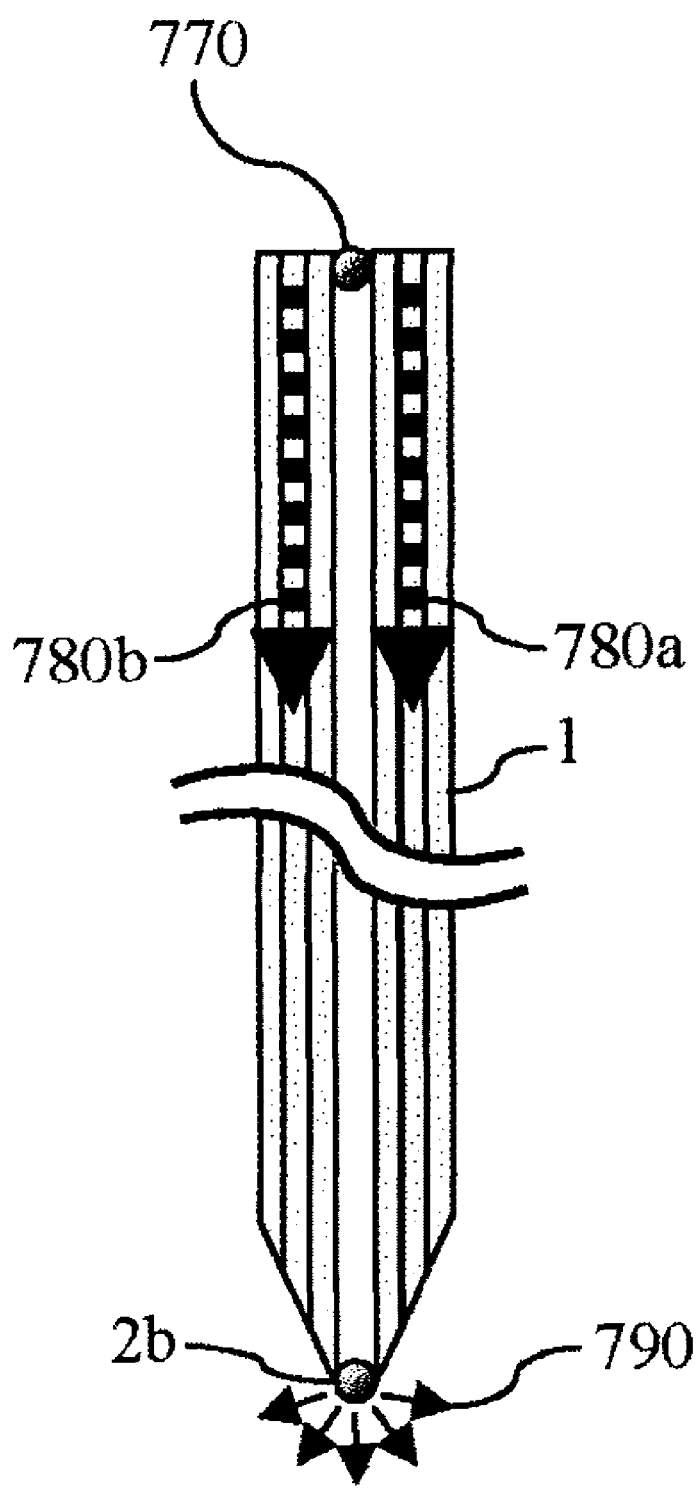
FIG. 29 is a frontal sectional diagram of a modification of a plasmon intensifying near-field probe modification in embodiment 6.
Figure 30:
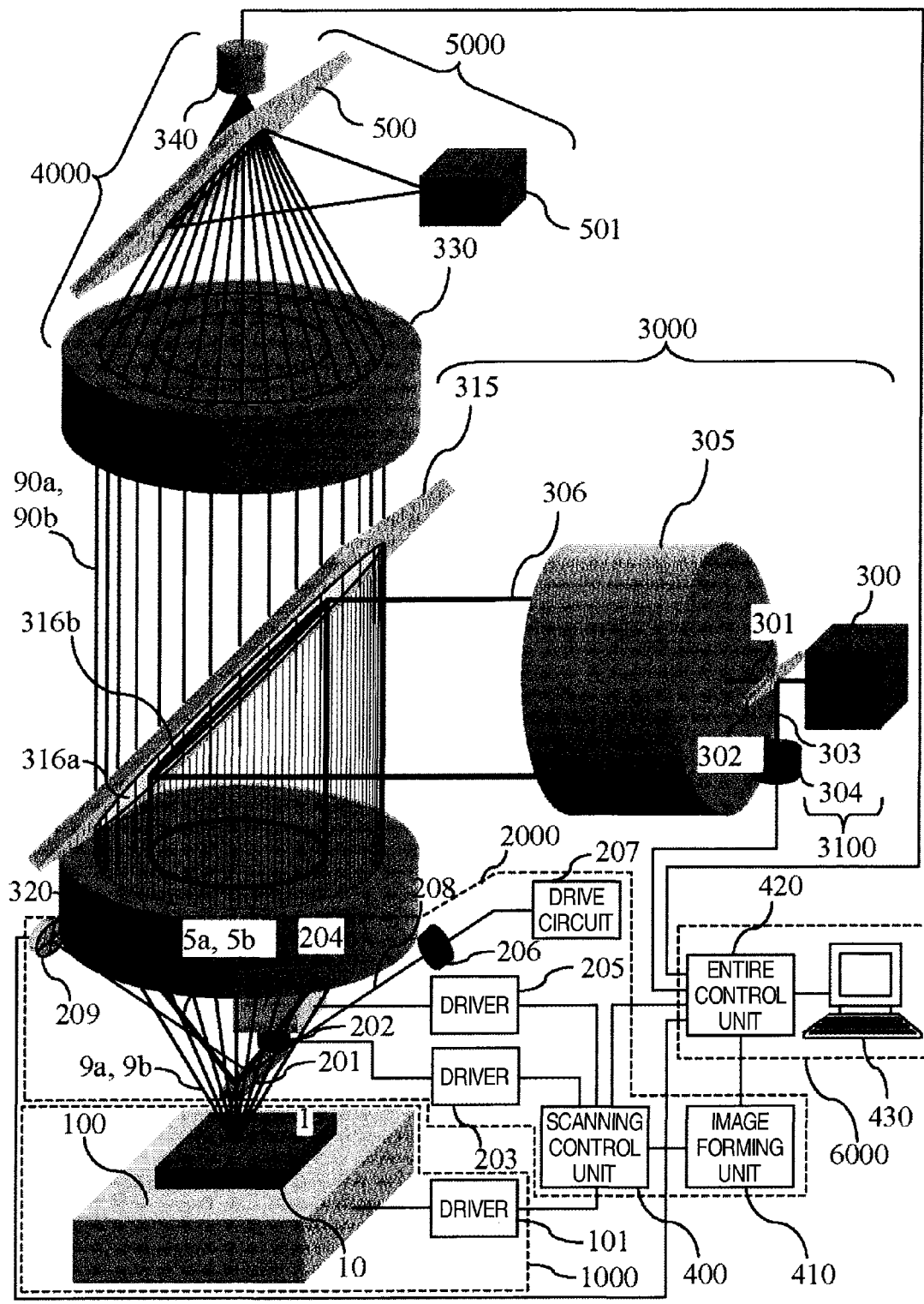
FIG. 30 is a block diagram showing schematic construction of a scanning probe microscope in embodiment 6.
Figure 31:
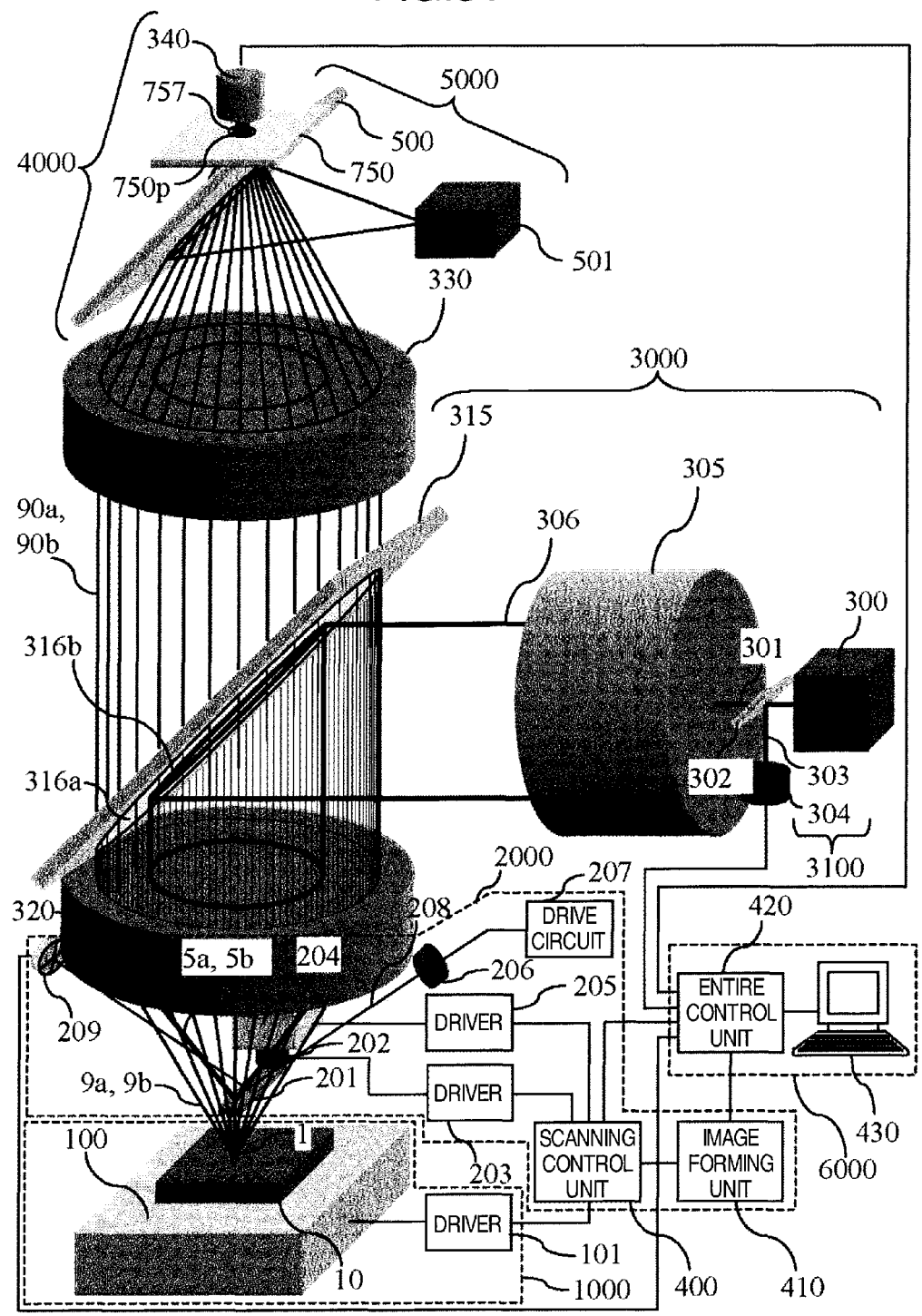
FIG. 31 is a block diagram showing the arrangement of pinhole light shield plate in a scanning probe microscope in embodiment 6.
Figure 32:
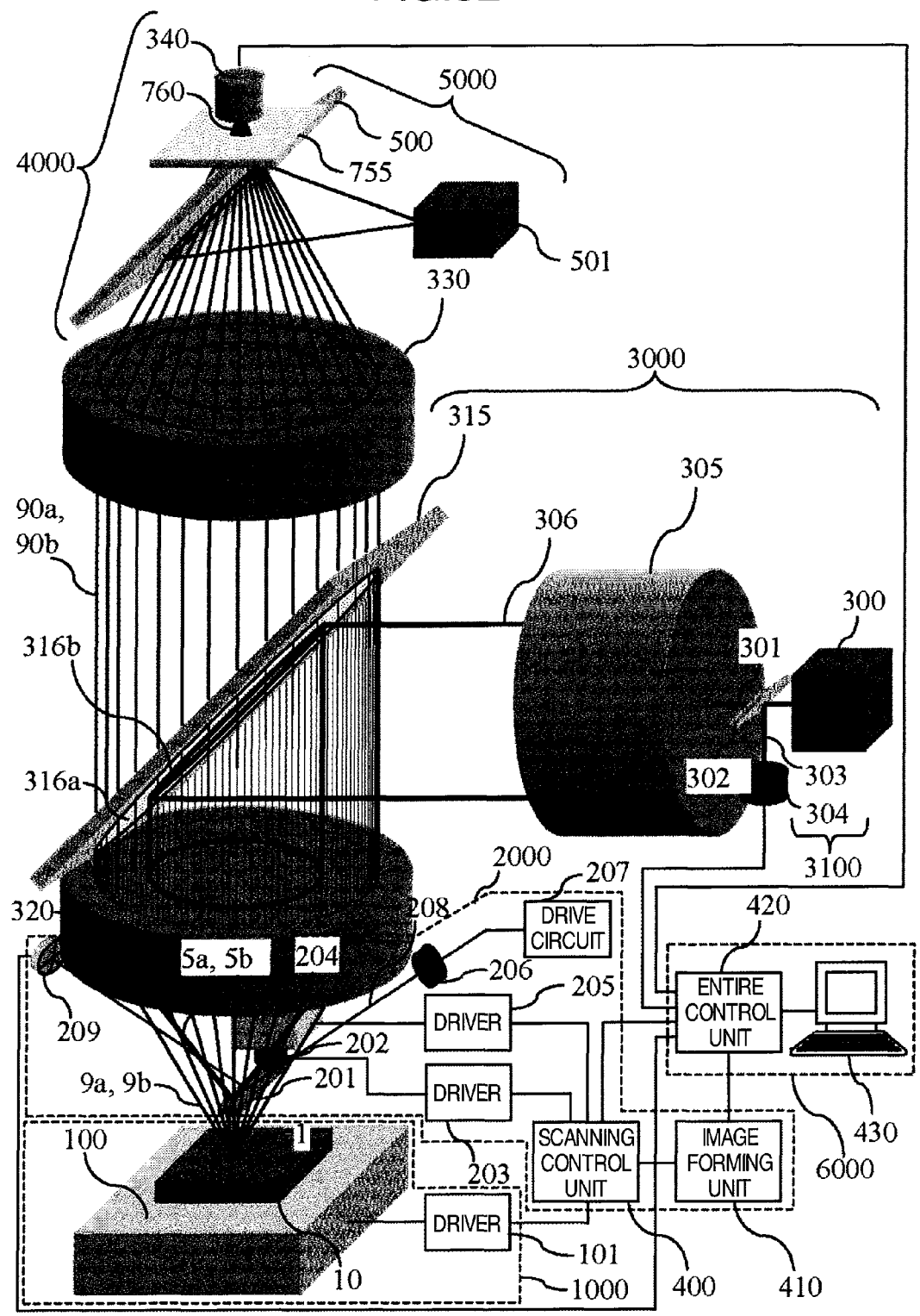
FIG. 32 is a block diagram showing the arrangement of a wavelength selection filter in a scanning probe microscope in embodiment 6.

The invention claimed is:

1. A scanning probe microscope comprising a measurement probe having its interior embedded with a metal structure, a cantilever for supporting said measurement probe, cantilever drive means for driving said cantilever to scan said measurement probe three-dimensionally in relation to an inspection objective sample, displacement detection means for detecting a deformation of said cantilever, and near-field optical image acquisition means for generating near-field light rays between said measurement probe embedded with the metal structure and the surface of said inspection objective sample and acquiring a near-field optical image of the surface of said inspection objective sample.

2. A scanning probe microscope according to claim 1 further comprising an AFM image generation means for generating an atomic force microscopic image (AFM image) of said inspection objective sample surface by processing a signal obtained by detecting a deformation of said cantilever with the help of said displacement detection means.

3. A scanning probe microscope according to claim 1, wherein said near-field optical image acquisition means includes a laser irradiation optical system for irradiating a laser beam on one end of said measurement probe embedded with the metal structure, near-field light ray detection optical system for detecting near-field light rays generated between the other end of said measurement probe and the surface of said inspection objective sample by causing the other end of said measurement probe to approach the surface of said inspection objective sample under the irradiation of the laser beam by said laser irradiation optical system, and a near-field optical image processing system for processing a signal obtained by detecting said near-field light rays with the help of said near-field light ray detection optical system to obtain a near-field optical image of said sample surface.

4. A scanning probe microscope according to claim 3, wherein the length of said measurement probe is adjusted such that near-field light rays of maximum intensity can be obtained in accordance with a wavelength of the laser beam irradiated from said laser irradiation optical system.

5. A scanning probe microscope according to claim 3, wherein said laser irradiation optical system further includes a polarization light ray control unit for controlling the state of polarization of a laser beam irradiating on one end of said measurement probe embedded with the metal structure.

6. A scanning probe microscope according to claim 3 wherein said laser irradiation optical system irradiates a white light laser beam on one end of said measurement probe embedded with the metal structure, said near-field light ray detection optical system detects near-field light rays generated between the other end of said measurement probe and the surface of said inspection objective sample by separating wavelengths of the near-field light rays, and said near-field optical image processing system processes individual signals detected through the wavelength separation to synthesize them, thus obtaining a color near-field ray optical image of the surface of said sample.

7. A scanning probe microscope according to claim 3, wherein said cantilever includes a light guide quarter of pyramid shape for guiding the beam from said laser irradiation optical system to said measurement probe.

8. A scanning probe microscope according to claim 7, wherein said near-field light ray detection optical system has a light shield plate for selectively passing the near-field light rays generated between the other end of said measurement probe and the surface of said inspection objective sample.

9. A scanning probe microscope according to claim 1, wherein said measurement probe is formed of a carbon nanotube or a metal nanotube and a gold particle or silver particle, or a gold rod or silver rod is embedded in the interior of the carbon nanotube or metal nanotube.

10. A scanning probe microscope according to claim 1, wherein said measurement probe is formed of a carbon nanotube or a metal nanotube, the tip end of the carbon nanotube or metal nanotube caused to approach the surface of said inspection objective sample is sharpened and a gold particle or silver particle is embedded in the tip end.

11. A scanning probe microscope according to claim 1, wherein said measurement probe is formed of a carbon nanotube or a metal nanotube, the carbon nanotube or metal nanotube has its upper end embedded with metal carbide or a fluorescent particle and has its lower end embedded with a gold particle or silver particle, or a gold rod or silver rod.

12. A method of observing a sample by using a scanning probe microscope in which a cantilever for supporting a measurement probe having its interior embedded with a metal structure is driven to scan said measurement probe three-dimensionally in relation to an inspection objective sample, a deformation of said cantilever due to the three-dimensional scan is detected, and a near-field optical image of the surface of said inspection objective sample is acquired by using said measurement probe embedded with the metal structure.

13. A sample observing method using a scanning probe microscope according to claim 12, wherein an atomic force microscopic image (AFM image) of said inspection objective sample surface by processing a signal obtained by detecting a deformation of said cantilever.

14. A sample observing method using a scanning probe microscope according to claim 12, wherein a near-field optical image of said sample surface is obtained by irradiating a laser beam on one end of said measurement probe embedded with the metal structure, detecting near-field light rays generated between the other end of said measurement probe and the surface of said inspection objective sample by causing the other end of said measurement probe to approach the surface of said inspection objective sample under irradiation of the laser beam, and processing a signal obtained by detecting the near-field light rays.

15. A sample observing method using a scanning probe microscope according to claim 14, wherein the length of said measurement probe is adjusted such that near-field light rays of maximum intensity can be obtained in accordance with a wavelength of the laser beam irradiated from said laser irradiation optical system.

16. A sample observing method using a scanning probe microscope according to claim 14, wherein the laser beam irradiated on one end of said measurement probe embedded with the metal structure is a laser beam the polarization state of which is controlled.

17. A sample observing method using a scanning probe microscope according to claim 14, wherein the laser beam irradiated on one end of said measurement probe embedded with the metal structure is a white light laser beam, near-field light rays generated between the other end of said measurement probe and the surface of said inspection objective sample are detected by separating wavelengths of the near-field light rays and a signal obtained through the wavelength separation detection is processed to obtain a colored near-field optical image of said inspection objective sample surface.

18. A sample observing method using a scanning probe microscope according to claim 12, wherein the near-field light rays are detected by using as said measurement probe a carbon nanotube or metal nanotube having its interior embedded with a gold particle or silver particle or a gold rod or silver rod.

19. A sample observing method using a scanning probe microscope according to claim 12, wherein the near-field light rays are detected by using as said measurement probe a carbon nanotube or metal nanotube having its upper end embedded with metal carbide or a fluorescent particle and having its lower end embedded with a gold particle or silver particle or a gold rod or silver rod.

20. A sample observing method using a scanning probe microscope according to claim 12, wherein said measurement probe is formed of a carbon nanotube or metal nanotube, the tip end of the carbon nanotube or metal nanotube caused to approach the surface of said inspection objective sample is sharpened and said tip end is embedded with a gold particle or silver particle.

* * * * *